US012651388B2

(12) United States Patent
Yaikhom

(10) Patent No.: US 12,651,388 B2
(45) Date of Patent: Jun. 9, 2026

(54) PRE-PROCESSING OF OCT B-SCANS FOR OCT ANGIOGRAPHY

(71) Applicant: OPTOS PLC, Dunfermline (GB)

(72) Inventor: Gagarine Yaikhom, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 477 days.

(21) Appl. No.: 18/108,103

(22) Filed: Feb. 10, 2023

(65) Prior Publication Data

US 2023/0298236 A1 Sep. 21, 2023

(30) Foreign Application Priority Data

Feb. 28, 2022 (EP) ..................................... 22159148

(51) Int. Cl.
| | |
|---|---|
| *G06T 11/60* | (2026.01) |
| *A61B 3/10* | (2006.01) |
| *A61B 3/12* | (2006.01) |
| *G16H 30/40* | (2018.01) |
| *G16H 50/50* | (2018.01) |

(52) U.S. Cl.
CPC .............. *G06T 11/60* (2013.01); *A61B 3/102* (2013.01); *A61B 3/1241* (2013.01); *G16H 30/40* (2018.01); *G16H 50/50* (2018.01); *G06T 2210/22* (2013.01)

(58) Field of Classification Search
CPC ......... A61B 3/102; A61B 3/1241; G06T 3/00; G06T 7/11; G06T 11/60; G06T 2207/10101; G06T 2207/20132; G06T 2207/30041; G06T 2207/30101; G06T 2210/22; G16H 30/40; G16H 50/50
See application file for complete search history.

(56) References Cited

U.S. PATENT DOCUMENTS

| | | |
|---|---|---|
| 10,010,249 B1 | 7/2018 | Sadda et al. |
| 2021/0090253 A1 | 3/2021 | Ellis |

FOREIGN PATENT DOCUMENTS

| | | |
|---|---|---|
| JP | 2010-110556 A | 5/2010 |
| JP | 2018-079208 A | 1/2022 |

(Continued)

OTHER PUBLICATIONS

JP Office Action Mailed on Feb. 27, 2024 for JP Application No. 2023020209, 5 page(s).

(Continued)

*Primary Examiner* — Jack Dinh
(74) *Attorney, Agent, or Firm* — Faegre Drinker Biddle & Reath LLP

(57) ABSTRACT

A computer-implemented method of processing repeat B-scans of an imaged region of a body part, the imaged region including an anatomical feature in a first subregion and vasculature of interest in a second subregion of the imaged region, to generate cropped B-scans for use in generating OCT angiography data which provides a representation of the vasculature of interest, the method comprising processing each B-scan of the repeat B-scans by: selecting a subset of the data elements of the B-scan such that the selected data elements are distributed along a representation of the anatomical feature in the B-scan; using the selected data elements to define a respective subregion of interest in the B-scan, which includes OCT data acquired from the second subregion containing the vasculature of interest; and cropping the B-scan to leave the subregion of interest in the B-scan.

11 Claims, 12 Drawing Sheets

(56)                     References Cited

FOREIGN PATENT DOCUMENTS

WO        2019/210079 A1    10/2019
WO        2021/113674 A1     6/2021

OTHER PUBLICATIONS

Extended European Search Report (EESR) dated Aug. 19, 2022 issued in European patent application 22 159 148.0 (10 sheets).
Turgut, B., "Optical Coherence Tomography Angiography—A General View", European Ophthalmic Review, 2016, vol. 10, pp. 39-42.
Chalam et al., "Optical Coherence Tomography Angiography in Retinal Diseases", Journal of Ophthalmic and Vision Research, 2016, 11, pp. 84-92.
Ruikang K. Wang et al., "Optical Coherence Tomography Angiography-Based Capillary Velocimetry", J. Biomed. Opt. 22(6), SPIE, 066008 (2017), pp. 066008 to 066008-13.
Gao et al., "Optical Coherence Tomography Angiography", Investigative Ophthalmology & Visual Science, 2016, vol. 57, No. 9 (10 sheets).
Gorczynska et al., "Comparison of Amplitude-Decorrelation, Speckle-Variance and Phase-Variance OCT Angiography Methods for Imaging the Human Retina and Choroid", Biomedical Optics Express 911, 2016, vol. 7, No. 3, pp. 911-942 (32 sheets).
Huang et al., "Optical Coherence Tomography Angiography Using the Optovue Device", OCT Angiography in Retinal and Macular Diseases, 2016, vol. 56, pp. 6-12 (7 sheets).
Kafieh et al., R. "A Review of Algorithms for Segmentation of Optical Coherence Tomography from Retina", J. Med. Signals Sens. Jan.-Mar. 2013, vol. 3, Issue 1, pp. 45-60.
Janpongsri et al., "Pseudo-real-time retinal layer segmentation for high-resolution adaptive optics optical coherence tomography", Journal of BIOphotonics, 2020, pp. 1-13.

Receive repeat B-scans
of the imaged region of the body part
acquired by an OCT imaging apparatus — S100

Process the repeat B-scans to generate
respective cropped B-scans — S200

Generate OCTA data
by processing the cropped B-scans — S300

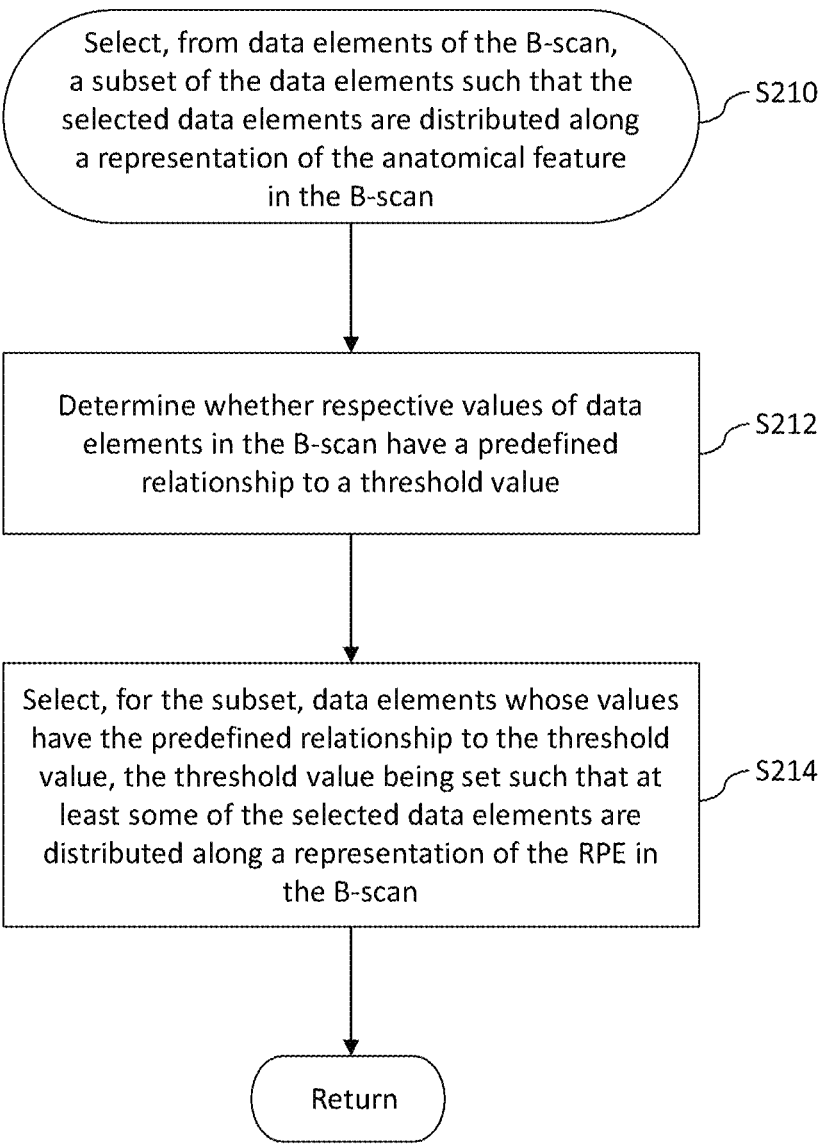

Select, from data elements of the B-scan,
a subset of the data elements such that the
selected data elements are distributed along
a representation of the anatomical feature
in the B-scan — S210

Determine whether respective values of data
elements in the B-scan have a predefined
relationship to a threshold value — S212

Select, for the subset, data elements whose values
have the predefined relationship to the threshold
value, the threshold value being set such that at
least some of the selected data elements are
distributed along a representation of the RPE in
the B-scan — S214

Return

Fig. 8

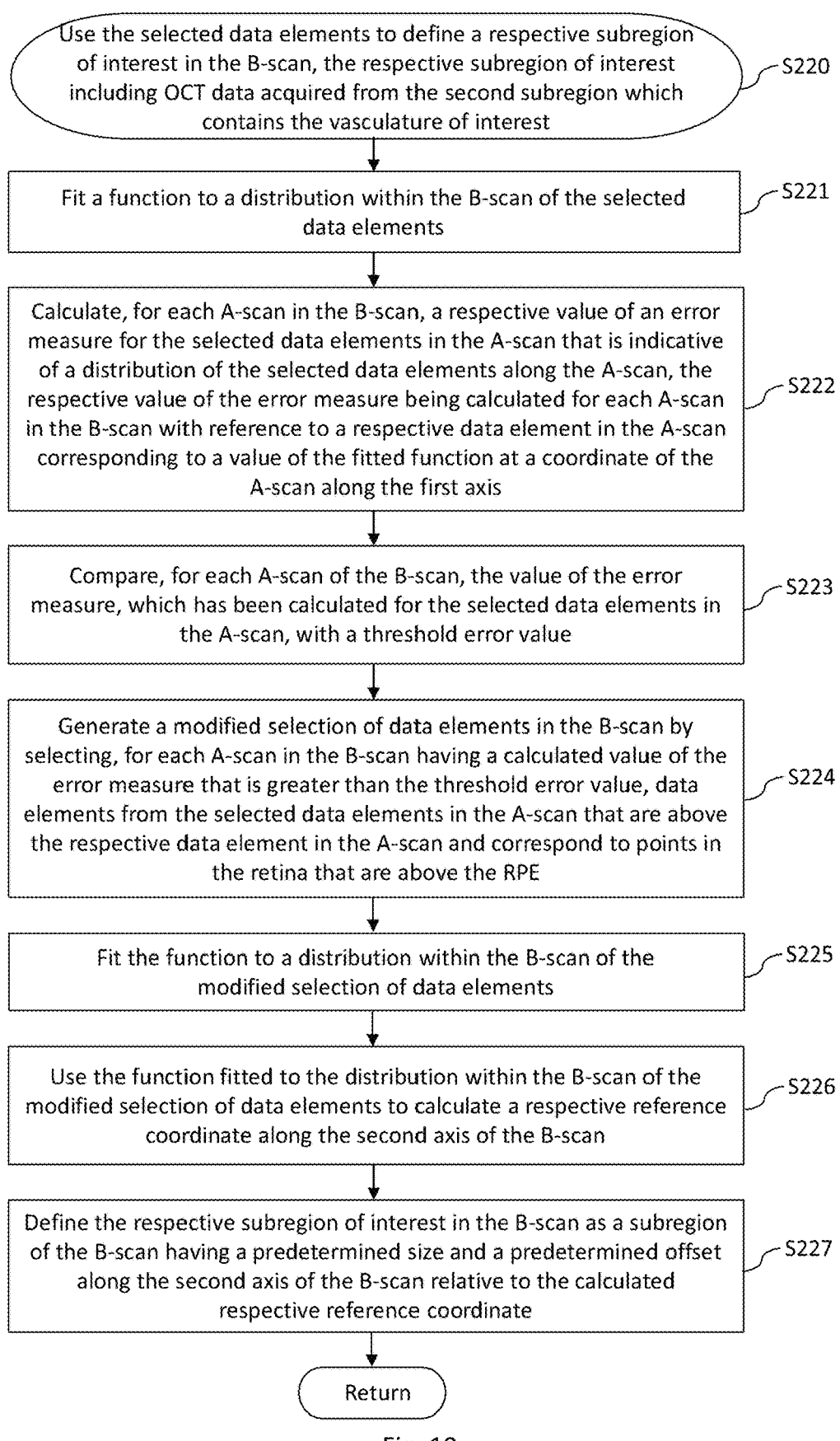

Use the selected data elements to define a respective subregion of interest in the B-scan, the respective subregion of interest including OCT data acquired from the second subregion which contains the vasculature of interest ⌐S220

Fit a function to a distribution within the B-scan of the selected data elements ⌐S221

Calculate, for each A-scan in the B-scan, a respective value of an error measure for the selected data elements in the A-scan that is indicative of a distribution of the selected data elements along the A-scan, the respective value of the error measure being calculated for each A-scan in the B-scan with reference to a respective data element in the A-scan corresponding to a value of the fitted function at a coordinate of the A-scan along the first axis ⌐S222

Compare, for each A-scan of the B-scan, the value of the error measure, which has been calculated for the selected data elements in the A-scan, with a threshold error value ⌐S223

Generate a modified selection of data elements in the B-scan by selecting, for each A-scan in the B-scan having a calculated value of the error measure that is greater than the threshold error value, data elements from the selected data elements in the A-scan that are above the respective data element in the A-scan and correspond to points in the retina that are above the RPE ⌐S224

Fit the function to a distribution within the B-scan of the modified selection of data elements ⌐S225

Use the function fitted to the distribution within the B-scan of the modified selection of data elements to calculate a respective reference coordinate along the second axis of the B-scan ⌐S226

Define the respective subregion of interest in the B-scan as a subregion of the B-scan having a predetermined size and a predetermined offset along the second axis of the B-scan relative to the calculated respective reference coordinate ⌐S227

Return

Fig. 10

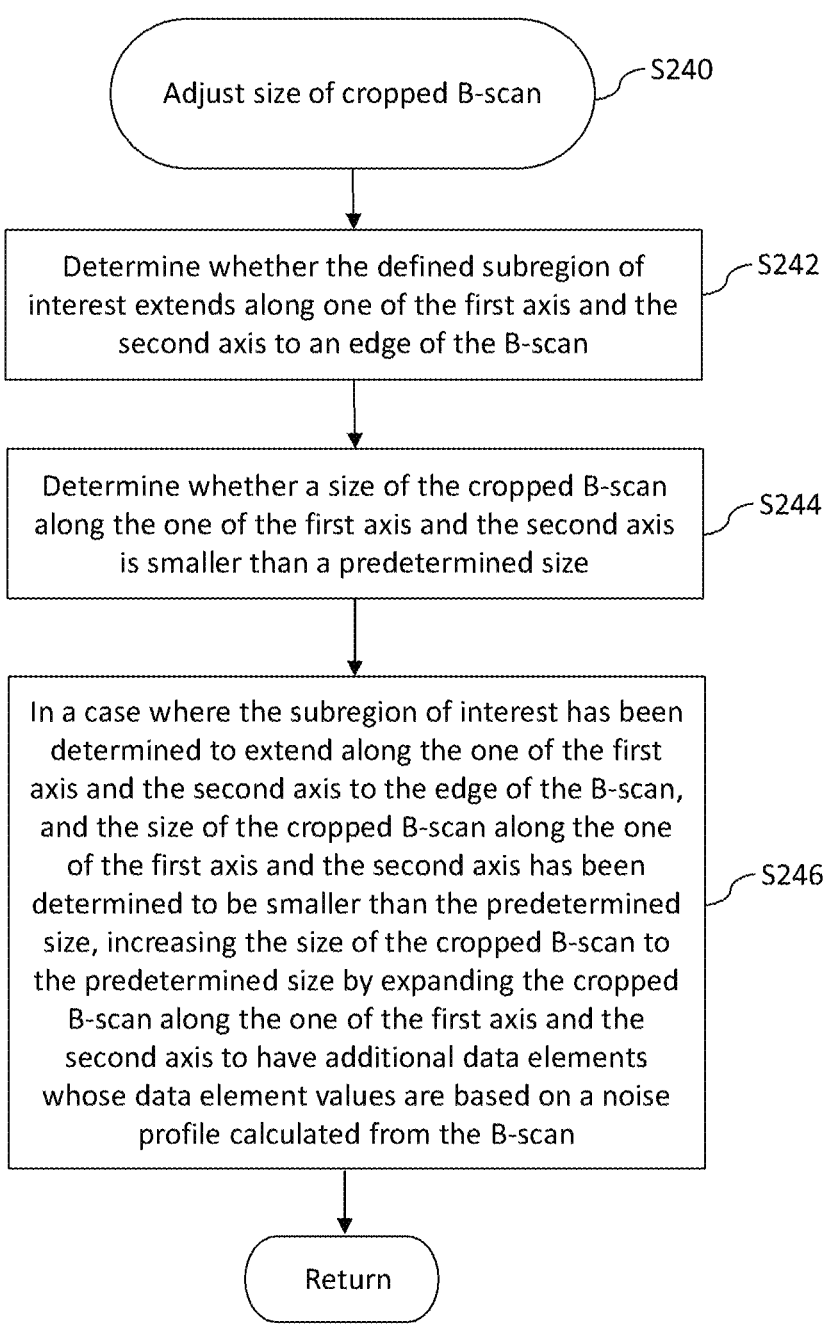

Adjust size of cropped B-scan — S240

Determine whether the defined subregion of interest extends along one of the first axis and the second axis to an edge of the B-scan — S242

Determine whether a size of the cropped B-scan along the one of the first axis and the second axis is smaller than a predetermined size — S244

In a case where the subregion of interest has been determined to extend along the one of the first axis and the second axis to the edge of the B-scan, and the size of the cropped B-scan along the one of the first axis and the second axis has been determined to be smaller than the predetermined size, increasing the size of the cropped B-scan to the predetermined size by expanding the cropped B-scan along the one of the first axis and the second axis to have additional data elements whose data element values are based on a noise profile calculated from the B-scan — S246

Return

Fig. 12

PRE-PROCESSING OF OCT B-SCANS FOR OCT ANGIOGRAPHY

This application claims the benefit of priority of European Patent Application No. EP 22 159 148.0 filed Feb. 28, 2022, the content of which is incorporated by reference herein in its entirety, as if set forth fully herein.

FIELD

Example aspects herein generally relate to the field of optical coherence tomography (OCT) and, more particularly, to the processing of repeat OCT B-scans of an imaged region of a body part to generate cropped B-scans for use in generating OCT angiography data which provides a representation of vasculature in the imaged region.

BACKGROUND

Optical coherence tomography angiography (OCTA) is a non-invasive imaging technique which uses low-coherence interferometry to obtain structural and functional (blood flow) information of an imaged body part in tandem, which has been used in various medical fields. In ophthalmology, for example, OCTA has been used to diagnose a variety of diseases such as age-related macular degeneration (AMD), diabetic retinopathy, artery and vein occlusions, sickle cell disease and glaucoma, for example.

OCTA compares differences in the backscattered OCT signal between repeat B-scans of a common OCT scan region of the body part (i.e. B-scans of the same cross-section of the body part, which have been acquired at different times) to construct a map of blood flow, and relies on the principle that parts of the OCT scan region containing moving red blood cells result in fluctuations in backscattered OCT signal over time, whereas much smaller fluctuations occur in the backscattered OCT signal from static parts of the OCT scan region, which contain no blood flow.

Several types of OCTA have been developed, which process repeat OCT scans in different ways to map the vasculature therein, for example split-spectrum amplitude decorrelation angiography (SSADA), optical microangiography (OMAG) and OCT angiography ratio analysis (OCT-ARA). A review of these types of OCTA and some of the OCTA systems which exist on the market is provided in "Optical Coherence Tomography Angiography-A General View" by Turgut, European Ophthalmic Review, 2016; 10(1): 39-42, the contents of which are incorporated herein by reference in their entirety.

SUMMARY

The present inventor has devised, in accordance with a first example aspect herein, a computer-implemented method of processing repeat B-scans of an imaged region of a body part acquired by an OCT imaging apparatus, the imaged region including an anatomical feature confined to a first subregion of the imaged region and vasculature of interest that is confined to a second subregion of the imaged region, to generate cropped B-scans for use in generating OCT angiography data which provides a representation of the vasculature of interest. The method comprises processing each B-scan of the repeat B-scans to generate a respective cropped B-scan by: selecting, from data elements of the B-scan, a subset of the data elements such that the selected data elements are distributed along a representation of the anatomical feature in the B-scan; using the selected data elements to define a respective subregion of interest in the B-scan, the respective subregion of interest including OCT data acquired from the second subregion which contains the vasculature of interest; and generating the respective cropped B-scan by cropping the B-scan to leave the subregion of interest in the B-scan.

Furthermore, the present inventor has devised, in accordance with a second example aspect herein, a computer-implemented method of generating optical coherence tomography angiography, OCTA, data which provides a representation of vasculature of interest in an imaged region of a body part. The method comprises: receiving repeat B-scans of the imaged region of the body part acquired by an optical coherence tomography imaging apparatus; processing the repeat B-scans to generate respective cropped B-scans in accordance with the method of the first example aspect set out above; and generating the OCTA data by processing the cropped B-scans.

The present inventor has also devised, in accordance with a third example aspect herein, a computer program comprising computer-readable instructions which, when executed by a computer, cause the computer to perform a method according to at least one of the first example aspect and the second example aspect set out above. The computer program may be stored on a non-transitory computer-readable storage medium (e.g. a CD or a memory stick) or carried by a signal (e.g. an Internet download).

The present inventor has further devised, in accordance with a fourth example aspect herein, an apparatus for processing repeat B-scans of an imaged region of a body part acquired by an OCT imaging apparatus, the imaged region including an anatomical feature confined to a first subregion of the imaged region and vasculature of interest confined to a second subregion of the imaged region, to generate cropped B-scans for use in generating OCT angiography data which provides a representation of the vasculature of interest. The apparatus comprises a selection module arranged to process each B-scan of the repeat B-scans by selecting, from data elements of the B-scan, a respective subset of the data elements such that the selected data elements are distributed along a representation of the anatomical feature in the B-scan. The apparatus further comprises a subregion defining module arranged to process each B-scan of the repeat B-scans by using the subset of data elements, which has been selected by the selection module from the data elements of the B-scan, to define a respective subregion of interest in the B-scan, the respective subregion of interest including OCT data acquired from the second subregion which contains the vasculature of interest. The apparatus further comprises a cropping module arranged to generate cropped B-scans by cropping each B-scan of the repeat B-scans to leave in the B-scan the respective subregion of interest defined for the B-scan by the subregion defining module.

The present inventor has further devised, in accordance with a fifth example aspect herein, an apparatus for generating optical coherence tomography angiography, OCTA, data which provides a representation of vasculature in an imaged region of a body part. The apparatus comprises a receiver module arranged to receive repeat B-scans of the imaged region of the body part acquired by an OCT imaging apparatus, and the apparatus according to the fourth example aspect as set out above, which is arranged to process the received repeat OCT B-scans to generate cropped B-scans. The apparatus for generating OCTA data further comprises an OCTA data generating module arranged to generate the OCTA data by processing the cropped B-scans.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

FIG. 8 is a flow diagram illustrating an example process by which the subset of data elements may be selected in process S210 of the flow diagram shown in FIG. 7.

FIG. 10 is a flow diagram illustrating a process by which the subregion defining module of the example embodiment defines the subregion of interest in the B-scan, in process S220 of FIG. 7.

FIG. 12 is a flow diagram illustrating a process by which the cropping module of the example embodiment adjusts the size of the cropped B-scan 310-1 shown in FIG. 3B.

DETAILED DESCRIPTION OF EXAMPLE EMBODIMENTS

Movements of the body part relative to the OCT imaging apparatus during acquisition of a sequence of repeat B-scans, which is to be processed to generate OCTA data, may cause offsets to occur between B-scans in the sequence, so that at least some of the repeat B-scans cover slightly different cross-sections of the body part. As the variations in the locations of static features of the body part caused by these offsets would have equivalent effect on the output of the OCTA data-generating algorithm to variations in locations of moving red blood cells among repeat B-scans that are perfectly aligned to one another, the movements of the body part during acquisition of the repeat B-scans would degrade the quality of the OCTA data and therefore needs to be accounted for.

Known OCT imaging apparatuses are often able to reduce lateral offsets between the repeat B-scans by tracking changes in the OCT scan location and making adjustments to the delivery of the OCT sample light based on these changes to compensate for deviations of the OCT scan location from a target OCT scan location. Image registration algorithms are often employed in known OCTA data-generating software to compensate for axial offsets between the repeat B-scans, and may also deal with any lateral offsets that have not been fully compensated for by the tracking/compensation functions of the OCT imaging apparatus. However, image registration algorithms may fail to converge to the correct result (or fail to converge at all) in case the axial shift between B-scans is large. This, in turn, may increase the failure rate of the OCTA data-generating software, which may lead to a perception of its inaccuracy or inadequacy.

The inventor has also recognised that, owing to the distribution of vasculature in imaged regions of body parts that is typically encountered in practical applications of OCTA, conventional approaches to storing repeat OCT B-scans for OCTA tends to not only be wasteful of data storage resources but also place unnecessarily high demands on the data processing and storage requirements of the OCTA data-generating algorithm used to generate the OCTA data from the B-scans. More particularly, the region of a body part covered in a repeat B-scan is usually much larger than a region of interest containing the vasculature that is to be mapped out by OCTA, and therefore tends to contain a lot of redundant information whose storage and processing is unnecessary for the generation of OCTA data.

Figure 3A:
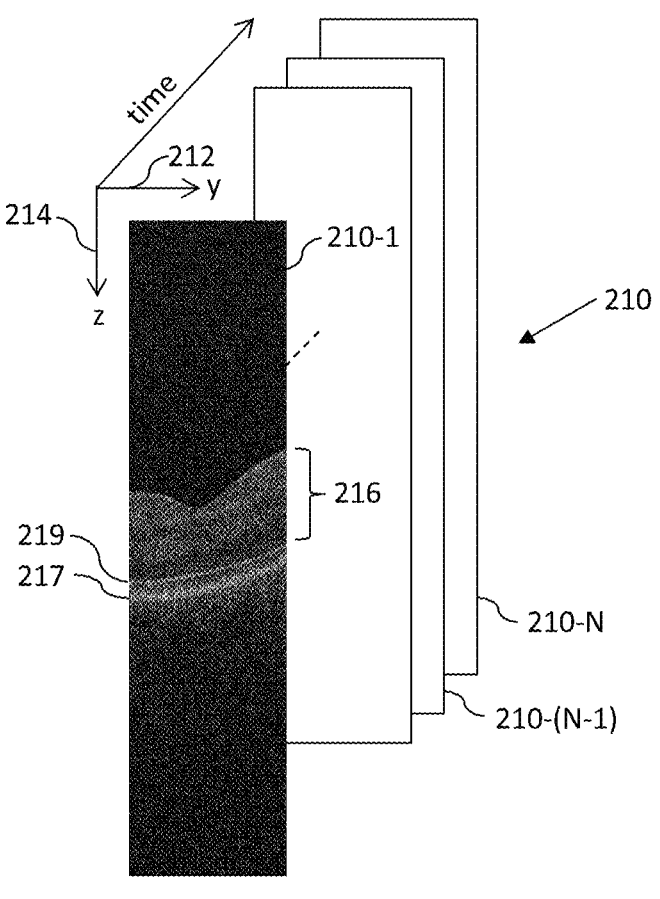
FIG. 3A is a schematic illustration of N repeat B-scans that have been acquired for one of the scan elevations shown in FIG. 2A at different times.

By way of an example, in the retinal B-scan 210-1 shown in FIG. 3A, the retinal vasculature is contained within a band of the B-scan 210-1 whose upper and lower bounds (not shown) correspond approximately to the upper and lower extents of the collection of grey regions that are shown against the dark background and near the middle of the B-scan 210-1 in FIG. 3A, which represent the layers of the retina including the nerve fibre layer (NFL) and the retinal pigment epithelium (RPE), whose representations in the B-scan 210-1 are shown within region 216 and at 217 in FIG. 3A, respectively. The darker regions of the B-scan 210-1 above and below this band (excluding the choriocapillaris and the choroid) are not useful for generating OCTA data relating to retinal vasculature. The region 216 comprises layers including, for example, the ganglion cell layer, inner plexiform layer and the NFL.

The inventor has recognised that the inclusion of the OCT data relating to these darker regions in the B-scan 210-1 causes several problems; it is wasteful of storage resources, it slows down and can reduce the reliability of the registration process described above (particularly where there is a large axial shift between repeat B-scans that are being registered with respect to each other), and its processing by the OCTA data-generating algorithm unnecessarily consumes valuable processor and memory resources. It should be noted that these problems are not specific to the processing of repeat OCT B-scans of the retina but arise in the processing of repeat OCT B-scans of other body parts, such as the skin, which may be processed to obtain OCTA data representing vasculature therein. Example embodiments described herein address at least some of the problems discussed above, and will now be described in detail by reference to the Figures.

Figure 1:
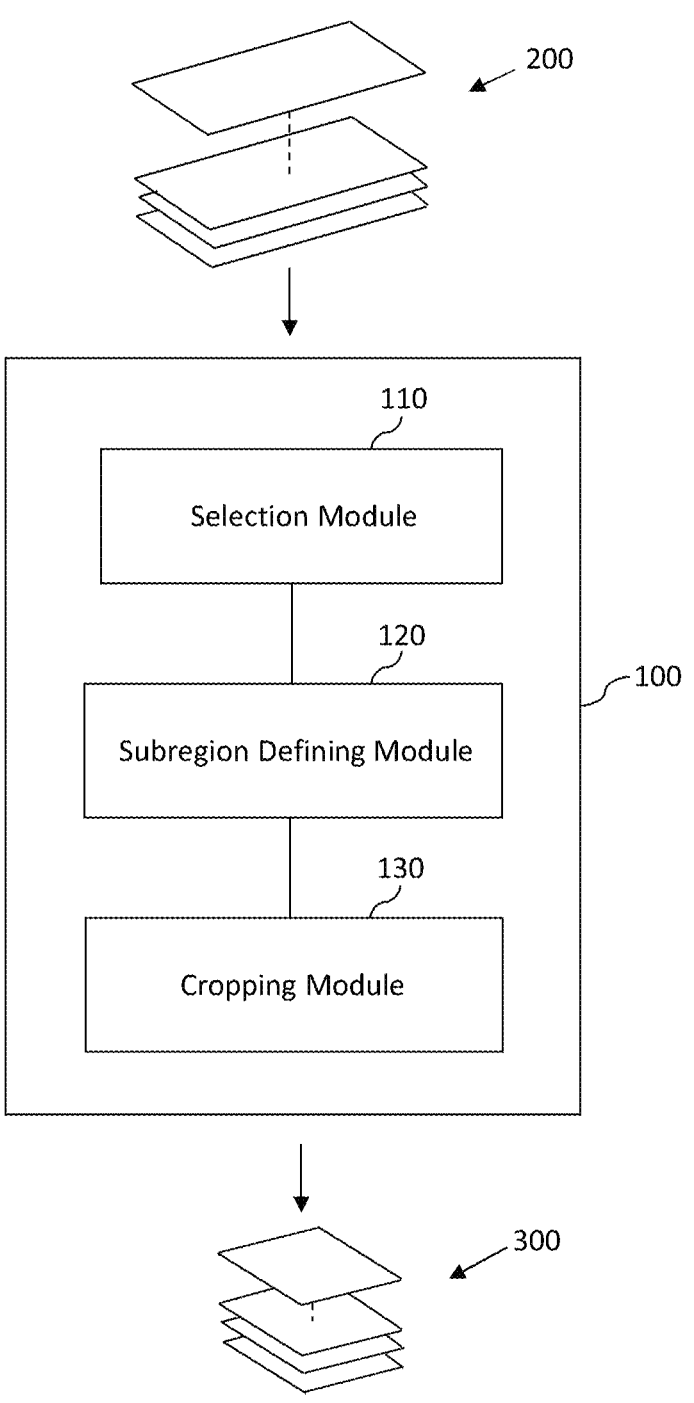
FIG. 1 is a schematic illustration of an apparatus of an example embodiment herein for processing repeat OCT B-scans of an imaged region of a body part to generate cropped B-scans for use in generating OCT angiography data.

FIG. 1 is a schematic illustration of an apparatus 100 according to an example embodiment herein, which is arranged to process repeat B-scans 200 of an imaged region of a body part acquired by an OCT imaging apparatus (not shown). The imaged region includes an anatomical feature which is confined to, and completely occupies, a first subregion of the imaged region. By way of an example, the anatomical feature may be an anatomical layer whose boundaries extend across the imaged region so as to span the imaged region, or it may alternatively be a boundary between a first anatomical layer and a second anatomical layer that extends across the imaged region so as to span the imaged region. The imaged region also includes vasculature of interest, which is confined to a second subregion of the imaged region. The first and second subregions may or may not overlap one another but have a spatial relationship to one another that is known (at least approximately) from the anatomy of the body part. The apparatus 100 processes the repeat B-scans 200 to generate respective cropped B-scans 300 for use in generating OCT angiography (OCTA) data, which provides a representation of the vasculature of interest.

The apparatus 100 may, by way of example and without limitation, process repeat B-scans 200 of a region of an eye that includes a portion of the retina, as in the present example embodiment, to generate cropped B-scans 300 of a subregion of the region that also includes the portion of the retina, which can be stored and shared in a more resource-efficient way, and which can allow known OCTA data-generating algorithms to generate a representation of retinal vasculature faster whilst using less working memory. Further, this reduction in the size of the OCTA volumes reduces the resource demand, required memory allocation and data transfer bandwidth within a given device deployment infrastructure, which can be particularly useful for cloud-based offerings. However, it will be appreciated that the B-scan processing techniques described herein are useful not only for processing retinal B-scans but also in the processing of B-scans of the skin or any other body part whose vasculature is to be mapped out by OCTA.

Figure 2A:
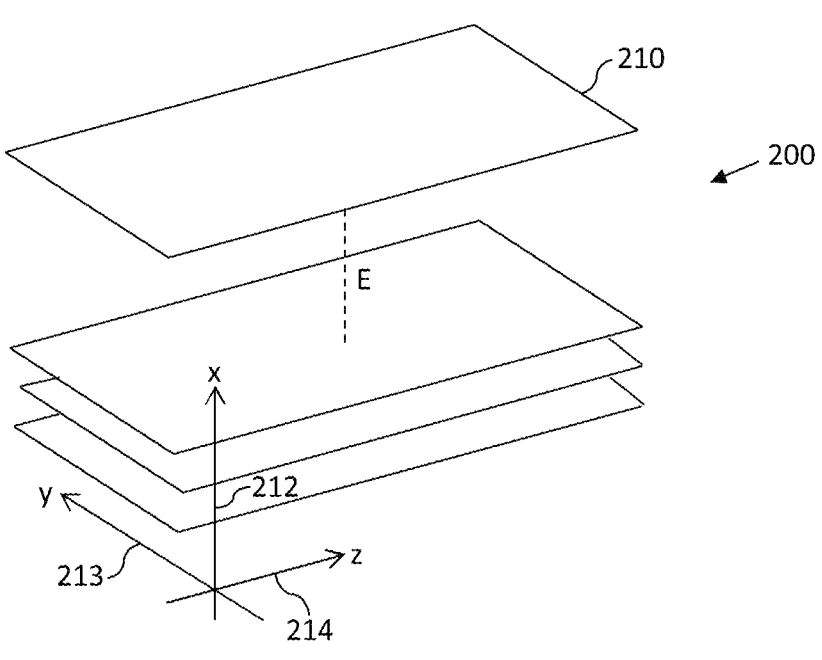
FIG. 2A is a schematic illustration of sets of repeat B-scans that have been acquired at different respective scan elevations.
Figure 2B:
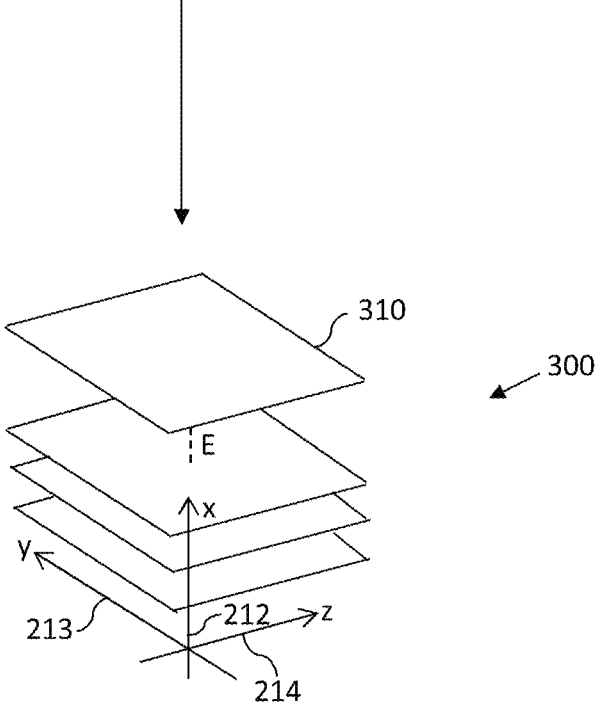
FIG. 2B is a schematic illustration of respective sets of cropped repeat B-scans that have been generated by the apparatus of the example embodiment processing the repeat B-scans illustrated in FIG. 2A.

FIG. 2A shows a schematic illustration of the repeat B-scans 200 that are to be processed by the apparatus 100. Each set of N repeat B-scans (also referred to herein as an "imaging slice") 210 is taken at a respective scan elevation of a number E of scan elevations along a first axis 212 (e.g. an x-axis of a Cartesian coordinate system), which is taken to extend within a surface of an approximately planar portion of the retina that lies in an imaged three-dimensional region of the eye (i.e. the surface of the retina adjacent to the vitreous humor of the eye). Each set of repeat B-scans 210 comprises a number N of B-scans covering a common two-dimensional region of the retina (which is a slice or cross-section through the imaged three-dimensional region) at the respective scan elevation that have been acquired at different times, where the common region extends along a second axis 213 (e.g. a y-axis of the Cartesian coordinate system) that is also within the surface of the retina, and along a third axis 214 (e.g. a z-axis of the Cartesian coordinate system) that is in a depth direction of the retina (i.e. in a direction that spans the depth of the retina from the vitreous humor to the choroid and sclera). The repeat B-scans 200 may, as in the present example embodiment, cover a region of the eye that includes a portion of the vitreous humor, a portion of the retina, and a portion of the sclera of the eye, which appear in this order along the z-axis direction of each B-scan.

FIG. 3A is a schematic illustration of the repeat B-scans within one of the sets of N repeat B-scans 210. The B-scans 210-1 to 210-N of the set of N repeat B-scans 210 shown in FIG. 3A are of the same slice through the retina of the eye but taken at a different times (as illustrated by their spacing along a time axis in FIG. 3A), such that the B-scans 210-1 to 210-N are temporally separated.

Each of the B-scans 210-1 to 210-N is defined by a two-dimensional array of data elements. In FIG. 3A, each of the B-scans 210-1 to 210-N comprises A-scans that are arrayed along a y-axis of the B-scan (also referred to herein as the "first axis of the B-scan", which coincides with axis 213 in this example), wherein each of the A-scans comprises data elements that are arrayed along a z-axis of the B-scan (also referred to herein as the "second axis of the B-scan", which coincides with axis 214 in this example). The value of each data element in any B-scan of the B-scans 210-1 to 210-N provides a respective interference signal measurement result acquired by the OCT imaging apparatus, and the location of the data element within the B-scan (as specified by the coordinate of the data element along the first axis of the B-scan, and the coordinate of the data element along the second axis of the B-scan) is indicative of a location, within the imaged three-dimensional region of the eye, at which the interference signal measurement was made. The data elements are commonly referred to as 'pixels' (in two-dimensional images) or 'voxels' (in three-dimensional volumes), and the data element values may be referred to as pixel or voxel intensities, or reflectance values.

Figure 3B:
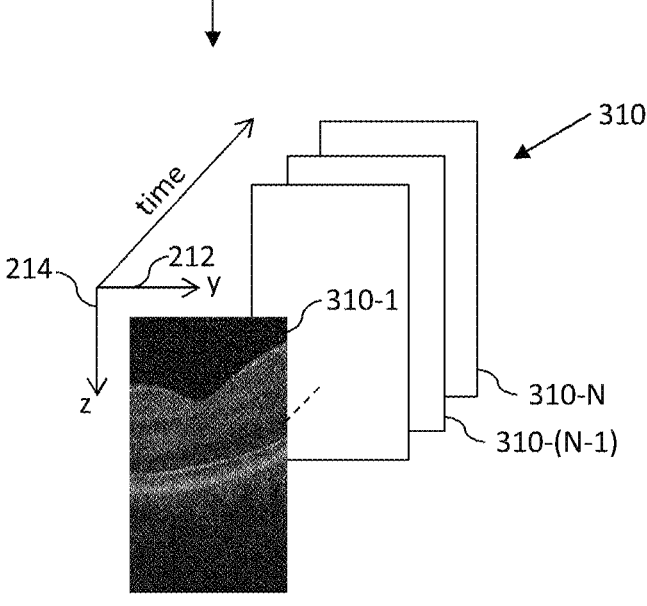
FIG. 3B is a schematic illustration of N cropped repeat B-scans that have been generated by the apparatus of the example embodiment processing the N repeat B-scans shown in FIG. 3A.

FIG. 3B illustrates a number N of cropped B-scans 310-1 to 310-N, which have been generated by the apparatus 100 processing the N repeat OCT B-scans 210-1 to 210-N from FIG. 3A. The N repeat OCT B-scans acquired for each scan elevation along the first (x-) axis 212 are similarly processed by the apparatus 100 to generate a respective set of cropped OCT B-scans.

The number N of repeat B-scans may be any integer greater than or equal to two. The value of N is typically chosen to strike a balance between the competing requirements for the OCTA data-generating algorithm to process a sufficiently large number of repeat B-scans, and the repeat B-scans to be taken over as short a time interval as possible to reduce the adverse effect of movements of the eye on the quality of the OCTA data. By way of an example, N=4 in the present example embodiment. It should be noted that the value of N can, in principle, vary among the sets of repeat B-scans 210-1 to 210-N but is generally common to all of the repeat B-scans 210-1 to 210-N.

The number of scan elevations E is, in general, an integer greater than or equal to one. Where E is greater than one, the repeat OCT B-scans form a repeat volumetric scan, also referred to herein as a repeat C-scan. It should be noted that the repeat B-scans within the repeat C-scan can be acquired in any order by the OCT imaging apparatus. For example, the repeat B-scans of each imaging slice may all be acquired before the repeat B-scans of an adjacent imaging slice (i.e. at the next scan elevation along the x-axis) are acquired by the OCT imaging apparatus. Alternatively, a single B-scan or a prescribed number of repeat B-scans may be acquired at each successive scan elevation, before the B-scan acquisition process is repeated to acquire further one or more B-scans at each successive scan elevation along the first axis 212 of the coordinate system so as to build up the repeat C-scan.

The OCT imaging apparatus used to acquire the repeat volumetric scan is not limited and may be of any type known to those versed in the art, for example a point-scan OCT imaging system, which can acquire an OCT image by scanning a laser beam laterally across a region of the eye. The OCT imaging system may alternatively be a parallel acquisition OCT imaging system, such as Full-Field OCT (FF-OCT) or Line-Field OCT (LF-OCT), which may offer superior A-scan acquisition rates (up to tens of MHz) by illuminating an area or a line on the sample, rather than scanning a single spot across the eye. In FF-OCT, a two-dimensional region of the eye is illuminated at the same time and the lateral positions across the region are concurrently captured using a photodetector array such as a high-speed charge-coupled device (CCD) camera. Where the OCT imaging system is a Full-field OCT, it may take the form of a full-field time-domain OCT (FF-TD-OCT) or full-field swept-source OCT (FF-SS-OCT), for example. In FF-TD-OCT, the optical length of the reference arm can be varied during a scan in order to image regions at different depths in the eye. Each frame captured by the high-speed camera in FF-TD-OCT therefore corresponds to a slice of the eye at a respective depth within the eye. In FF-SS-OCT, the sample region is full-field illuminated using a swept light source that emits light whose wavelength varies over time. As the wavelength of the swept light source is swept over a range of optical wavelengths, a spectrogram correlating reflectivity information against optical wavelength can be generated by the high-speed camera for each camera pixel. Each frame captured by the camera therefore corresponds to reflectivity information for a single wavelength of the swept light source. Upon acquiring a frame for every wavelength of the swept light source, a C-scan of the region can be obtained by performing a Fourier transform on the samples of spectrograms generated by the camera. In line-field OCT (LF-OCT), a line of illumination may be provided to the sample and a B-scan may be acquired in the imaging process. Line-field OCT may be classified as line-field time-domain OCT (LF-TD-OCT), line-field swept-source OCT (LF-SS-OCT), or line-field spectral-domain OCT (LF-SD-OCT), for example.

Figure 4:
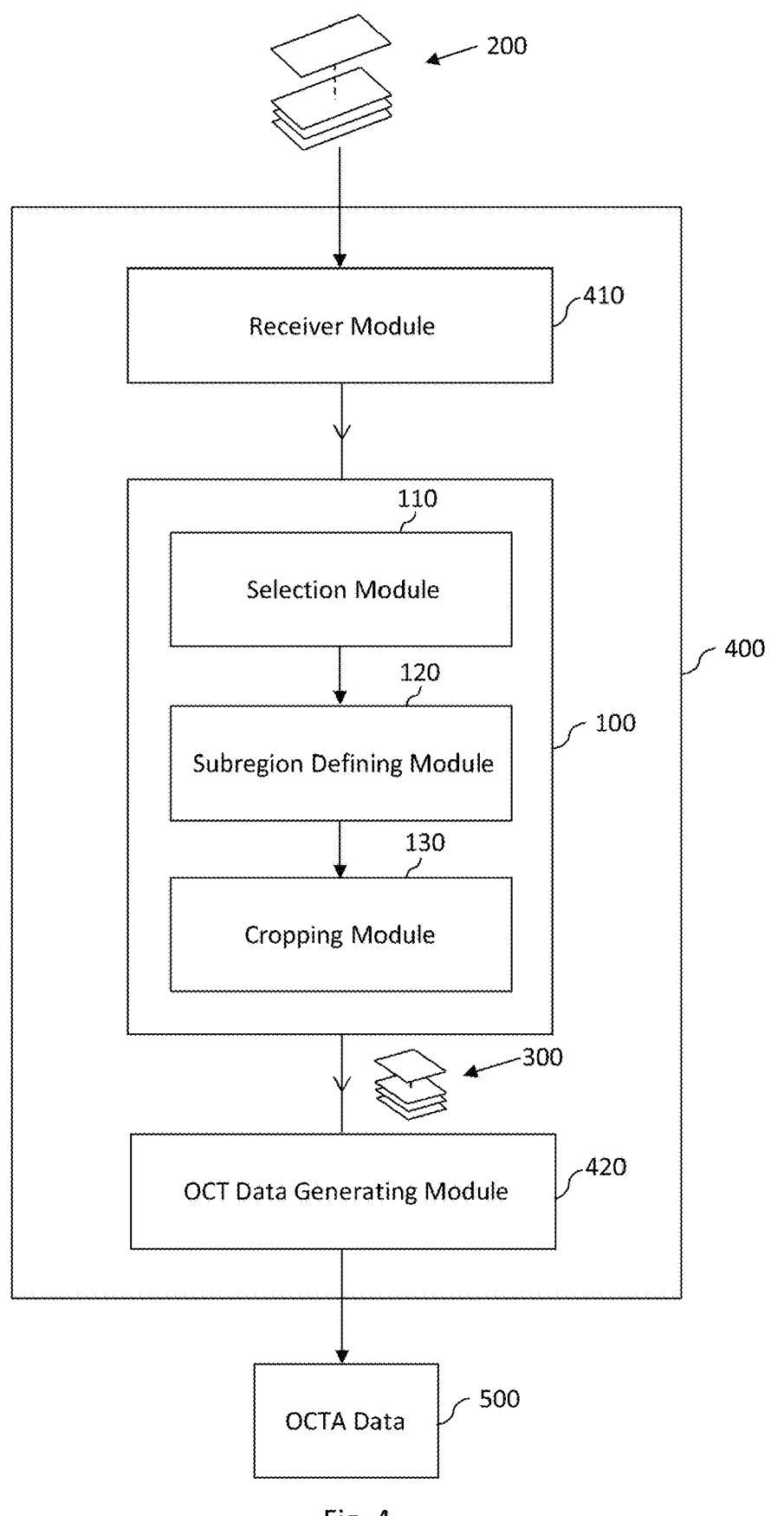
FIG. 4 is a schematic illustration of an apparatus for generating OCTA data representing vasculature in an imaged region of a body part, which includes the apparatus of the example embodiment for processing repeat OCT B-scans of the imaged region.

The apparatus 100 may be provided as a stand-alone data processor such as a PC, a laptop computer, tablet computer or the like, which may be communicatively coupled to the OCT imaging apparatus (directly or via a network, such as the Internet) to receive repeat B-scan data therefrom. Alternatively, the apparatus 100 may be provided as part of the OCT imaging apparatus, which may be of any known kind, as discussed above. The apparatus 100 may additionally or alternatively be provided as part of an apparatus 400 for generating OCTA data 500, as illustrated schematically in FIG. 4. The apparatus 400 of the example embodiment shown in FIG. 4 further comprises a receiver module 410, which is arranged to receive repeat B-scans 200 of a retina of an eye (or other imaged region of a body part) that have been acquired by an OCT imaging apparatus. The apparatus 400 also has an OCTA data generating module 420, which is arranged to generate the OCTA data 500 by processing the cropped B-scans 300 that have been generated by the apparatus 100 processing the repeat B-scans 200.

As illustrated in FIG. 1, the apparatus 100 comprises a selection module 110, a subregion defining module 120, and a cropping module 130, which are communicatively coupled to each other to exchange data as described below.

Figure 5:
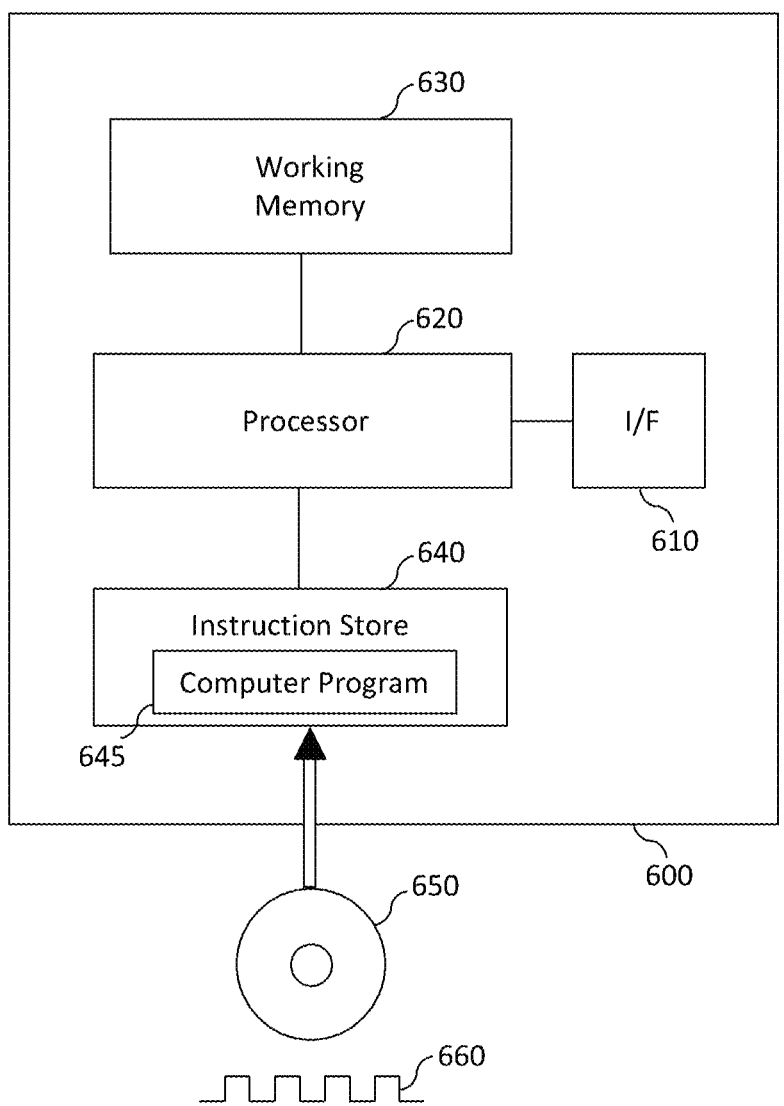
FIG. 5 illustrates an example hardware implementation of the apparatus of the example embodiment, in a programmable signal processing apparatus.

FIG. 5 is a schematic illustration of a programmable signal processing hardware 600, which may be configured to process repeat B-scans 200 using the techniques described herein and which can function as the selection module 110, the subregion defining module 120 and the cropping module 130 of the example embodiment. The programmable signal processing hardware 600 may further be configured to provide the functionalities of the receiver module 410 and the OCTA data generating module 420, thus providing a hardware implementation of the apparatus 400 for generating OCTA data 500 of the example embodiment shown in FIG. 4. The programmable signal processing apparatus 600 comprises a communication interface (I/F) 610, for receiving repeat B-scans 200 and outputting the generated OCTA data 500 and/or a graphical representation of the OCTA data 500 for displaying on a display, such an LCD screen or the like. The signal processing apparatus 600 further comprises a processor (e.g. a Central Processing Unit, CPU, and/or a Graphics Processing Unit, GPU) 620, a working memory 630 (e.g. a random access memory) and an instruction store 640 storing a computer program 645 comprising the computer-readable instructions which, when executed by the processor 620, cause the processor 620 to perform various functions including those of the selection module 110, the subregion defining module 120 and the cropping module 130, the receiver module 410 and the OCTA data generating module 420 described herein. The working memory 630 stores information used by the processor 620 during execution of the computer program 645. The instruction store 640 may comprise a ROM (e.g. in the form of an electrically erasable programmable read-only memory (EEPROM) or flash memory) which is pre-loaded with the computer-readable instructions. Alternatively, the instruction store 640 may comprise a RAM or similar type of memory, and the computer-readable instructions of the computer program 645 can be input thereto from a computer program product, such as a non-transitory, computer-readable storage medium 650 in the form of a CD-ROM, DVDROM, etc. or a computer-readable signal 660 carrying the computer-readable instructions. In any case, the computer program 645, when executed by the processor 620, causes the processor 620 to perform a method of processing repeat B-scans 200 to generate cropped repeat B-scans 300 as described herein. In other words, the apparatus 100 of the example embodiment may comprise a computer processor 620 and a memory 640 storing computer-readable instructions which, when executed by the computer processor 620, cause the computer processor 620 to perform a method of processing the repeat B-scans 200 to generate cropped B-scans 300 for use in generating OCTA data 500 as described below.

It should be noted, however, that one or more of the selection module 110, the subregion defining module 120 and the cropping module 130 (and the receiver module 410 and the OCTA data generating module 420, where included) may alternatively be implemented in non-programmable hardware, such as an application-specific integrated circuit (ASIC) or a field-programable gate array (FPGA).

Figure 6:
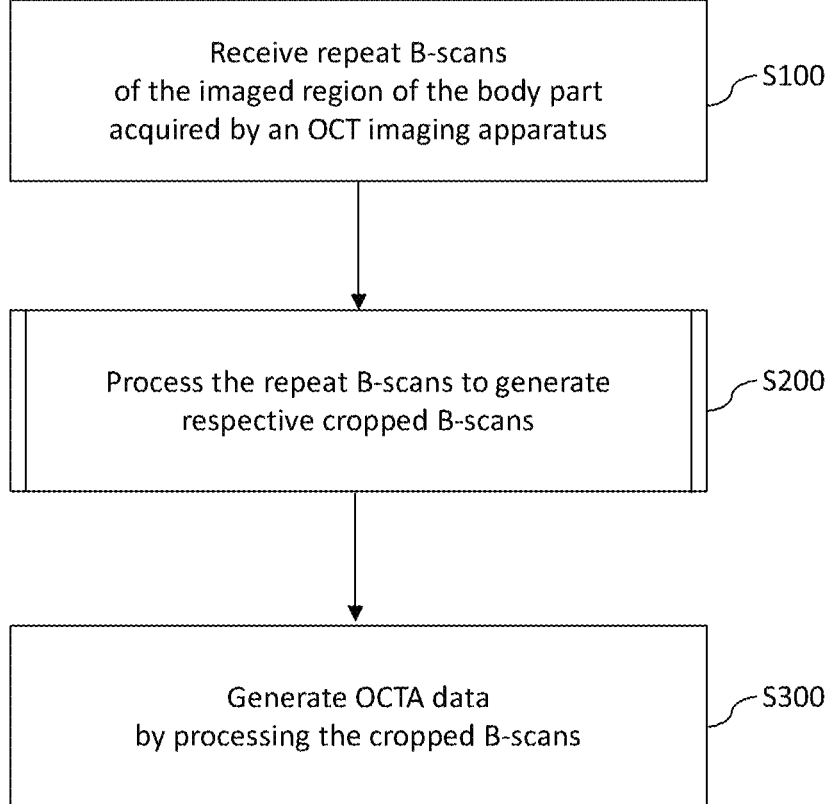
FIG. 6 is a flow diagram illustrating a method by which the apparatus of the example embodiment shown in FIG. 4 processes repeat OCT B-scans to generate OCTA data.

FIG. 6 is a flow diagram illustrating a method by which the apparatus 400 of the present example embodiment processes repeat OCT B-scans 200 to generate OCTA data 500.

In process S100 of FIG. 6, the receiver module 410 receives repeat B-scans 200 of the imaged region of the body part (e.g. a retina of an eye), as described above, which have been acquired by an OCT imaging apparatus.

In process S200 of FIG. 6, the apparatus 100 forming part of the apparatus 400 for generating OCTA data processes the repeat OCT B-scans 200 to generate cropped repeat B-scans 300 as described in more detail below.

In process S300 of FIG. 6, the OCTA data generating module 420 of the apparatus 400 generates the OCTA data 500 by processing the cropped repeat B-scans 300. The OCTA data generating module 420 may generate the OCTA data 500 using any known OCTA data generating method, for example an OCTA data generating method used in split-spectrum amplitude-decorrelation angiography (SSADA), optical microangiography (OMAG) or OCT angiography ratio analysis (OCTARA), or a known OCTA data generating method based on speckle variance, phase variance or correlation mapping. A review of these types of known OCTA data generating methods is provided in "Optical Coherence Tomography Angiography-A General View" by Turgut, European Ophthalmic Review, 2016; 10(1): 39-42, the contents of which are incorporated herein by reference in their entirety.

As cropped repeat B-scans 300, each containing only the respective region of interest that has been cropped from the originating B-scan, are used to generate the OCTA data 500 (rather than the entire repeat B-scans 200, which contain, in addition to the region of interest which contains voxels where OCTA signals are likely to be detected, a large amount of additional OCT data from parts of the imaged region containing no vasculature), the OCT data 500 can be generated more quickly, due to the relatively small size of OCTA volume formed by the cropped repeat B-scans 300. Reducing the size of the OCTA volume also reduces processor and memory requirements of the OCTA data generating algorithm, as well as the amount of space required for storing the OCTA volume for future use, thereby reducing resource demand on the deployment infrastructure. The reduction in storage requirements and a consequent reduction in data transfer bandwidth may be particularly beneficial in cloud-based implementations of the apparatus 400.

Furthermore, as the region of interest in each of the cropped repeat B-scans 300 is defined in the same way, using data elements that are distributed along a representation of the same anatomical feature that is present in all of the B-scans 200, as described below, the cropped repeat B-scans 300 generally have smaller axial shifts (along the z-axis of the B-scan) relative to one another than the originating repeat B-scans 200, which can be quickly and reliably corrected by the image registration algorithms discussed above.

Figure 7:
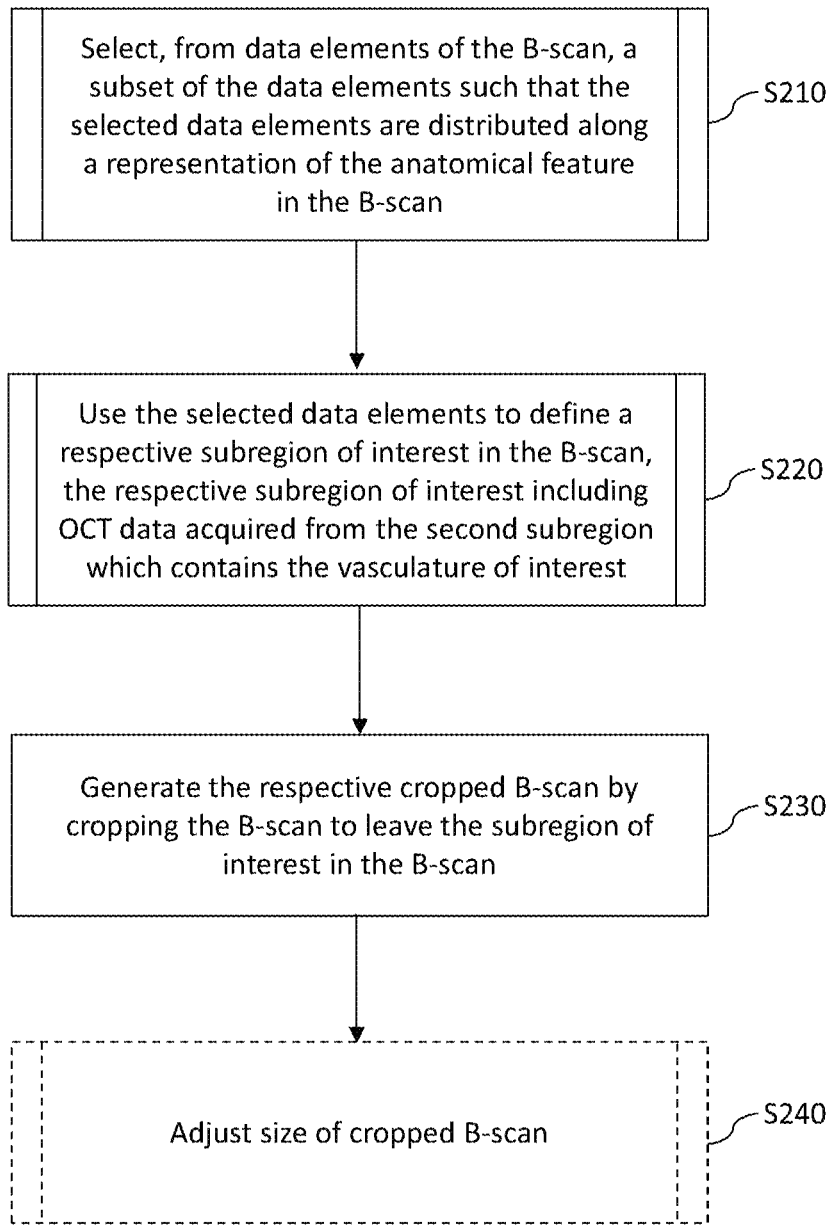
FIG. 7 is a flow diagram illustrating how the apparatus of the example embodiment shown in FIG. 1 processes repeat B-scans to generate cropped B-scans for use in generating OCTA data which represents vasculature of interest.

FIG. 7 is a flow diagram illustrating in more detail how the apparatus 100 of the example embodiment processes the repeat B-scans 200 in process S200 of FIG. 6 to generate cropped B-scans 300 for use in generating OCTA data 500 which represents vasculature of interest in the imaged region. The apparatus 100 attempts to process each B-scan of the repeat B-scans 200 in accordance with processes S210 to S230, and optional process S240 shown in FIG. 7, so as to generate a respective cropped version of the B-scan. However, it should be noted that, owing to factors such as image quality, the apparatus 100 may not succeed in cropping all of the input repeat B-scans 200, and some of the input repeat B-scans 200 may instead be discarded. The following description of FIG. 7 refers to the processing of B-scan 210-1 shown in FIG. 3A, which is taken by way of an example.

The anatomical feature included in the imaged region may be any anatomical layer of the retina that can be identified in the B-scan 210-1 using techniques known to those versed in the art. However, the anatomical feature is preferably the RPE, as illustrated in FIG. 3A. The RPE has an advantage of having a representation 217 in OCT reflectance B-scans that shows relatively little variation in its geometry (curvature), reflectance intensity and density among different subjects, and its typical appearance in B-scans allows it to be extracted using computationally efficient image processing techniques. By choosing a largely invariant anatomical feature such as the RPE, the techniques described herein may be used to reliably crop from B-scans certain regions of interest, which are predicted to contain OCT data for extracting vasculature by use of known OCTA data-generating algorithms, from a variety of subjects, without the need to perform calibration on a subject-by-subject basis.

Referring to FIG. 7, in process S210, the selection module 110 selects, from data elements of the B-scan 210-1, a (proper) subset of the data elements such that data elements in the subset are distributed along a representation of the anatomical feature in the B-scan 210-1, namely the representation of the RPE, which is shown at 217 in FIG. 3A. In other words, the selection module 110 selects, from among the data elements in the B-scan 210-1, a smaller number of data elements which define the representation 217 of the RPE in the portion of the retina (the remaining data elements, which have not been selected, not representing the RPE). The selected data elements have respective data element values that satisfy a predetermined criterion, such that the selected data elements are distributed along the representation 217 of the RPE (or another anatomical feature) in the B-scan 210-1.

In more detail, as illustrated in the flow diagram of FIG. 8 (which provides an example of how process S210 in FIG. 7 may be performed), the selection module 110 determines, in process S212, whether respective values of data elements in the B-scan 210-1 have a predefined relationship to a predefined threshold value (as an example of the predetermined criterion). More particularly, the selection module 110 may, as in the present example embodiment, determine in process S212 whether respective values of data elements in the B-scan 210-1 are greater than the predefined threshold value.

Then, in process S214 of FIG. 8, the selection module 110 selects, for the subset, data elements whose values have been determined in process S212 to have the predefined relationship to the threshold value, the threshold value being set such that at least some of the selected data elements are distributed along a representation 217 of the RPE in the B-scan 210-1. More particularly, the selection module 110 may, as in the present example embodiment, select in process S214 of FIG. 8, for the subset, data elements whose values are greater than the predefined threshold value.

The selection module 110 may, as in the present example embodiment, save the row (as abscissa, y) and column (as ordinate, z) values of the data elements selected in process S214 of FIG. 8 into a list of (y, z) coordinates. The row is the pixel index in the horizontal (first (y-) axis) direction of the B-scan 210-1, and the column is the pixel index in the axial (second (z-) axis) direction of the B-scan 210-1. The origin may be placed at the top-left corner of the B-scan 210-1. Thus, the column and row indices may be treated as (y, z) coordinates in a Cartesian coordinate system.

It should be noted, however, that the coordinates of the selected data elements (pixels) may be specified in other ways, for example by rotating the B-scan 210-1 90 degrees clockwise before processing so that the data elements selected in process S214 of FIG. 8 may have coordinates different from the ones described above. The coordinates of the selected data elements may be specified in any coordinate system that allows the curve-fitting of the anatomical feature in the B-scan 210-1 (in the present example embodiment, the RPE of the retina) described below to be carried out. The example embodiment may therefore employ an alternative coordinate system for specifying the coordinates of the data elements selected by the selection module 110, for example a coordinate system obtained by rotating the coordinate system of the example embodiment, and/or flipping it vertically and/or horizontally. Any affine transformation that preserves the relationship between the positions in the B-scan 210-1 of the selected data elements may be applied.

It should be appreciated that the predefined relationship of a data element value to the predefined threshold value in the present embodiment is given by way of example only, and that the predefined relationship may alternatively be that data element value is smaller than (or smaller than or equal to) the predefined threshold value, for example. This alternative form of the predefined relationship may be used in cases where the B-scan 210-1 has been inverted so that dark pixels become light pixels, and vice versa. The predefined relationship between data element value and predefined threshold value may generally be set (at least in part) in dependence on the nature of the B-scans (e.g. depending on how the OCT measurement values are mapped to data element values) such that the data elements selected by the selection module 110 in process S210 of FIG. 7 are distributed along the representation 217 of the RPE in the B-scan 210-1.

The predefined threshold value may, as in the present example embodiment, be calculated from data element values of the M data elements that form the B-scan 210-1 such that there is only a predetermined number, n, of the data elements above a number, k, of standard deviations, S, from a mean, u, of the data element values in the B-scan 210-1, wherein k is set such that at least some of the selected data elements are distributed along the representation of the RPE 217 in the B-scan 210-1. In the present example embodiment, the threshold value is calculated by modelling the data element values in the B-scan to be distributed in accordance with a predetermined type of statistical distribution, and determining (e.g. using known numerical methods) the value of an upper limit of an integral of the distribution (from zero) that yields a value of (M−n). In other words, the threshold is determined such that n selected data elements of the B-scan have a data element value above a threshold value of $\mu+k\cdot S$, wherein k is a user configurable parameter which may be set such that at least some of the pixels along the representation of the RPE 217 in the B-scan 210-1 are selected. The value of k can be determined via calibration through sample C-scans captured by the OCT imaging apparatus and is the same for the processing of all of the B-scans 200. The value of k may be determined based on practical requirements, with the objective of making trade-offs concerning performance and accuracy. One way of performing the calibration is to reduce the curve-fitting time by reducing the number of data elements n so that it is less than an empirically determined value which keeps the curve-fitting time below a maximum allowed by the design of the system. After processing representative sample C-scans, a value of k may be selected which keeps the curve-fitting time below the maximum allowed by system design. Several such practical considerations would affect the calibration of k.

In the present example embodiment, the data element values (or 'pixel intensities') in the B-scan are distributed in accordance with the Rayleigh distribution, as the reflectance is calculated as the modulus of the complex OCT signal produced by the inverse Fast-Fourier Transform of the OCT interferogram from the OCT imaging apparatus. Although the threshold value may be calculated more accurately by modelling the data element values in the B-scan 210-1 to be distributed in accordance with the Rayleigh distribution, a Gaussian distribution is assumed in the present example embodiment instead, as this may allow the threshold value to be determined in a more computationally efficient way and therefore provides a good practical trade-off. It should be noted that the data element value distribution may be modelled by a distribution type other than the Rayleigh and Gaussian types, for example a Beta distribution, a Chi-squared distribution or a Poisson distribution (among others).

Figure 9:
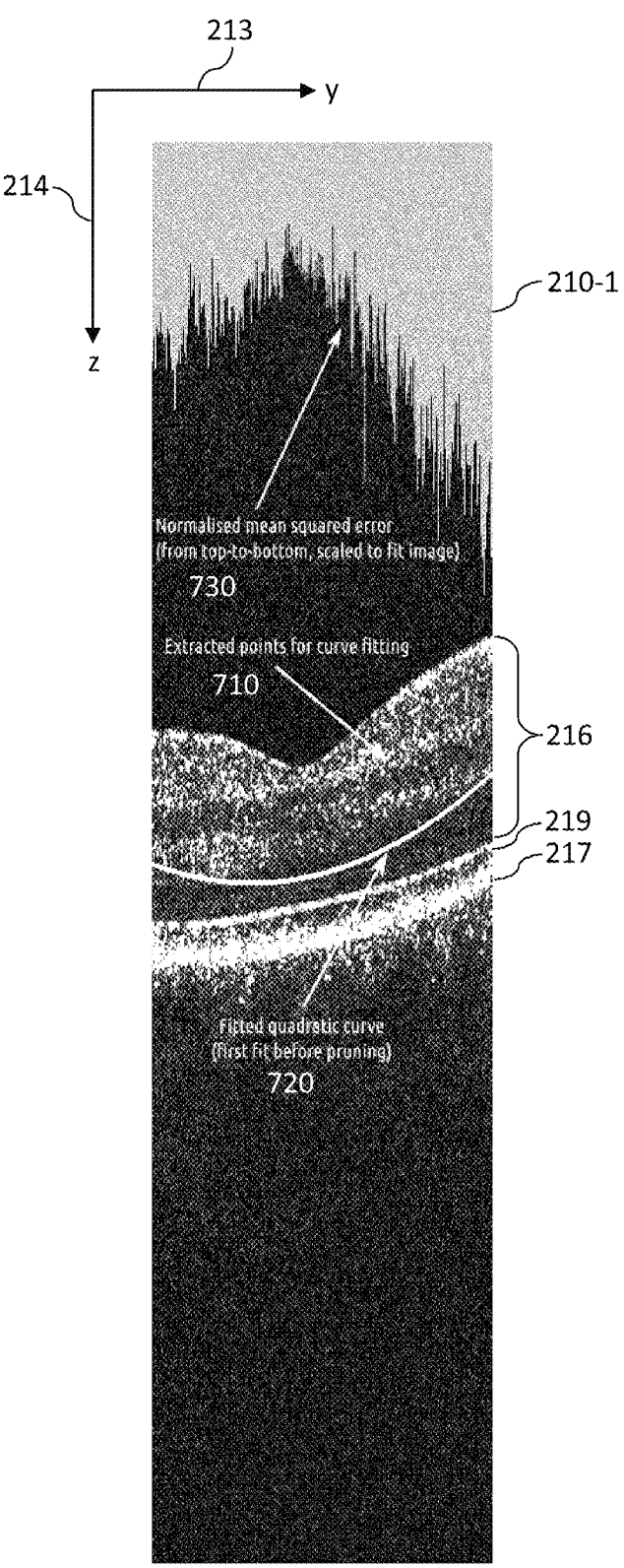
FIG. 9 shows an example of data elements that have been selected by the selection module of the example embodiment processing the B-scan of FIG. 3A, in process S210 of FIG. 7.

FIG. 9 shows an example of data elements 710 that have been selected by the selection module 110 processing the B-scan 210-1 of FIG. 3A, in process S210 of FIG. 7. As shown in FIG. 9, the selected data elements 710 provide representations of both the RPE (shown at 217 in FIG. 9) and the NFL (within 216 in FIG. 9).

Referring again to FIG. 7, in process S220, the subregion defining module 120 uses the data elements selected in process S210 to define a respective subregion of interest in the B-scan 210-1, specifically by using the selected data elements to provide a frame of reference for defining the location of the region of interest in the B-scan 210-1. Thus, for the B-scan 210-1 of an imaged (physical) region of the body part, which includes the anatomical feature that is confined to a first subregion of the imaged region, and the vasculature of interest that is confined to a second subregion of the imaged region, the subregion of interest defined in process S220 of FIG. 7 is a subregion of the B-scan 210-1 in which OCT data relating to the vasculature of interest is expected (from common knowledge of the anatomy of the body part) to be found. The subregion of interest thus includes OCT data acquired from the second (physical) subregion of the imaged region of the body part, which contains the vasculature of interest. In this way, the subregion defining module 120 uses a detectable representation of a (preferably invariant) anatomical feature in the B-scan 210-1 to define a subregion of interest in the B-scan 210-1, in which the vasculature of interest (generally detectable only from the processing of multiple repeat B-scans by known algorithms for generating OCTA data) is expected to be found.

In the present example embodiment, in which the imaged region of the body part comprises the retina of an eye, and the anatomical feature comprises an anatomical layer of the eye (preferably the RPE), the subregion defining module 120 uses the data elements selected in process S210 to define a subregion of interest in the B-scan 210-1, which is centred on the RPE along the second axis of the B-scan 210-1 (as described below), and whose size along the second axis is such that the subregion of interest contains within it the entire cross-section of the retina imaged in the B-scan 210-1. The subregion of interest, which is to be cropped from the remainder of the B-scan 210-1 that does not contain OCT data useful for OCTA, therefore contains OCT data derived from measurements of the retinal vasculature, which is to be processed by any known OCTA data-generating algorithm (together with OCT data from other repeat scans of the imaged region) to generate a representation of the retinal vasculature in the imaged region of the retina.

When processing each B-scan of the repeat B-scans 200, the subregion defining module 120 may use the selected data elements to define the respective subregion of interest in the B-scan by (i) using the selected data elements to determine at least one reference location indicator, which is/are indicative of a location of the representation of the RPE (or other chosen anatomical feature) in the B-scan, and (ii) defining a respective subregion of interest in the B-scan with respect to the location of the representation of the anatomical feature in the B-scan indicated by the at least one reference location indicator. More particularly, when processing each B-scan of the repeat B-scans 200, the subregion defining module 120 may, as in the present example embodiment, use the selected data elements to define the respective subregion of interest in the B-scan by (i) using the selected data elements to determine a respective reference location indicator, which is indicative of a location of the representation of the RPE (or other chosen anatomical feature) in the B-scan, and (ii) defining a respective subregion of interest in the B-scan with respect to the location of the representation of the anatomical feature in the B-scan indicated by the respective reference location indicator.

Step (i) can be performed in various different ways, for example by the subregion defining module 120 determining, as the reference location indicator for the B-scan being processed, a mean of the coordinate values of the selected data elements along the second (z-) axis of the B-scan, i.e. a mean of the selected data elements' z-axis coordinate values. Another example implementation of step (i), which is used in the example embodiment, is described below.

In step (ii), the subregion defining module 120 may, as in the present example embodiment, define the respective subregion of interest in the B-scan as a subregion of the B-scan having a predetermined offset along the second (z-) axis of the B-scan relative to the reference location indicator determined (by any technique) for the B-scan, and preferably having a fixed size. In general, the size of the subregion of interest need not be fixed, and may vary among at least some of the processed B-scans.

The process by which the subregion defining module 120 uses the data elements selected in process S210 of FIG. 7 to define a respective subregion of interest in the B-scan 210-1 in process S220 of FIG. 7 in the present example embodiment will now be described with reference to FIG. 10. FIG. 10 provides an example of how the process of S220 in FIG. 7 may be performed.

In process S221 of FIG. 10, the subregion defining module 120 fits a quadratic function to the spatial distribution of the selected data elements within the B-scan 210-1. In the example B-scan 210-1 of FIG. 9, the fitted quadratic function is illustrated by quadratic curve 720. Where the anatomical feature is the RPE of the retina, as in the present example embodiment, the subregion defining module 120 preferably performs a quadratic fit to the selected data elements, as the RPE in healthy eyes is normally parabolic, with a positive curvature. However, a polynomial of higher degree, which could over-fit the data, or even a linear fit that is less accurate, could alternatively be used by the subregion defining module 120 to fit the selected data elements. The function used for the curve fitting will determine the accuracy of the fit, and therefore the accuracy of the cropping of the B-scan 210-1 described below. As a result of performing process S221 in FIG. 10, values of coefficients $a_1$, $b_1$, and $c_1$ to satisfy the equation $z=a_1 y^2+b_1 y+c_1$ are determined by the subregion defining module 120.

The subregion defining module 120 may evaluate a statistical measure for goodness-of-fit of the function to the spatial distribution of the selected data elements in the B-scan 210-1 (i.e. a goodness-of-fit metric such as the average absolute residual, the average squared residual, the residual standard deviation or the coefficient of determination ($R^2$), for example), and generate a flag or other indicator which may be stored in the apparatus 100 (e.g. in the working memory 630) in association with the B-scan 210-1 and indicates that the B-scan 210-1 should be inspected, in case the poor curve fitting is caused by a disease that has distorted the RPE so that its shape deviates from the parabolic form that is expected for all healthy eyes. For instance, Choroidal Neo-Vascularisation (CNV) and Age-related Macular Degeneration (AMD) are diseases that could distort the shape of the retina, and therefore the shape of the RPE. The indicator generated by the subregion defining module 120 may cause a warning (in the form of a graphic displayed on a display (e.g. LCD screen) connected to the apparatus 100, or an audio signal emitted by a speaker connected to the apparatus 100, for example) to be notified to a user of the apparatus 100, to prompt the user to inspect the B-scan 210-1 for signs of disease. The warning may be notified to the user either at the time of process S221 of FIG. 10 being performed or later, when the repeat B-scans 200 or OCTA data 500 generated therefrom are being inspected by the user, for example.

Provided that the fit of the quadratic function to the spatial distribution of the selected data elements is satisfactory (which may be determined by evaluating a goodness-of-fit metric for the fitted function, and determining that the fit is satisfactory when the evaluated goodness-of-fit metric exceeds a predetermined threshold, for example), the function coefficients $a_1$, $b_1$, and $c_1$ acquired by the subregion defining module 120 in process S221 of FIG. 10 can be used to calculate a reference coordinate along the z-axis of the B-scan 210-1 that is indicative of a location of the RPE along this axis of the B-scan 210-1. To estimate the top extent of the RPE in the B-scan 210-1, the maximum of $z_1$ and $z_2$ is taken, where $z_1=c_1$ and $z_2=a_1 \cdot (w-1)^2+b_1 \cdot (w-1)+c_1$ are respectively the estimated RPE locations for the left-most (y=0) and right-most (y=w−1) columns of the B-scan 210-1. Here, column indexing is taken to being at 0, and the width (the number of columns, i.e. number of A-scans) of the B-scan 210-1 is denoted by w. To estimate the bottom extent of the RPE in the B-scan 210-1, the value of z for a column of the B-scan 210-1, where the derivative of the quadratic curve is minimum, is obtained. For healthy retinas, because of the positive curvature of the retina, the minimum point will occur at $y=-b_1/(2 \cdot a_1)$. The subregion defining module 120 calculates the reference coordinate along the z-axis of the B-scan 210-1 as a mean of the top and bottom extents of the RPE in the B-scan 210-1.

More generally, the subregion defining module 120 may use the fitted function to calculate the respective reference coordinate along the second axis of the B-scan 210-1 by determining a maximum value of the fitted function in an interval along the first axis spanned by the A-scans of the B-scan 210-1, determining a minimum value of the fitted function in the interval along the first axis, and calculating, as the reference coordinate, a mean of the maximum value and the minimum value.

The subregion defining module 120 may then define the subregion of interest in the B-scan 210-1 as a subregion of the B-scan 210-1 having a predetermined size and a predetermined offset along the z-axis of the B-scan 210-1 relative to the calculated reference coordinate. The size of the region of interest along the z-axis of the B-scan 210-1 and the offset of the region of interest relative to the reference coordinate along the z-axis may be predetermined from common knowledge of the anatomy of the eye and, in particular, how the vasculature in the retina is typically distributed relative to the RPE in the depth direction of the retina. In this way, the subregion defining module 120 may define a rectangular subregion of interest in the form of a band extending horizontally across the B-scan 210-1, whose upper and lower edges are parallel to the y-axis of the B-scan 210-1 and span the B-scan 210-1, the band having a size along the z-axis of the B-scan 210-1 and a location along the z-axis of the B-scan 210-1 such that it contains OCT data acquired from the second subregion of the imaged region of the eye discussed above, which contains the retinal vasculature of interest.

However, in the present example embodiment, the fit of the quadratic function to the spatial distribution of the selected data elements performed in process S221 of FIG. 10 is not satisfactory, as can be seen from fitted quadratic curve 720 in FIG. 9. This is because process S210 of FIG. 7 has resulted in the selection module 110 selecting data elements of the B-scan 210-1 within region 216, as well as those representing the RPE 217, due to these regions having data element values which both satisfy the value of the threshold used in process S210 in places. In particular, the data elements representing the NFL within region 216 are selected as they have data element values very similar to those of the RPE 217. This may not be desirable, as the inclusion of the data elements from region 216 along with the data elements representing the RPE reduces the quality of the quadratic curve fitting performed by the subregion defining module 120. The representation of at least the NFL within region 216 is furthermore not invariant in OCT B-scans of the retinas of different subjects. The fitted quadratic curve 720 consequently does not follow the shape of the RPE well, as can be seen in FIG. 9. As a consequence, the process for calculating the reference coordinate along the z-axis of the B-scan 210-1 described above would not provide an accurate indication of the location of the RPE (and therefore the centre of the retina) along the z-axis of the B-scan 210-1 in this case.

It should be noted, however, that B-scan 210-1 has been given by way of an example only, and that the NFL may not be as prominent, or not present at all, in other B-scans (depending on the setup of the OCT imaging apparatus) so that the subregion defining module 120 may define the subregion of interest in the B-scan 210-1 using the quadratic curve fitted in process S221 of FIG. 10, as described above.

To determine a quadratic function that provides a better fit to the representation 217 of the RPE in B-scan 210-1, the subregion defining module 120 of the present example embodiment generates a modified selection of data elements, to which the quadratic function can again be fitted.

Referring again to FIG. 10, in process S222, the subregion defining module 120 generates the modified selection of data elements firstly by calculating, for each A-scan in the B-scan 210-1, a respective value of an error measure for the data elements in the A-scan selected in process S210 of FIG. 7, which is indicative of a spatial distribution of the selected data elements along the A-scan. The subregion defining module 120 calculates the respective value of the error measure for each A-scan in the B-scan 210-1 with reference to a respective data element in the A-scan that corresponds to a value of the fitted function at a coordinate of the A-scan along the first (y-) axis of the B-scan 210-1. In other words, the fitted quadratic function obtained in process S221 of FIG. 10 is evaluated at a coordinate of the first axis of the B-scan 210-1, at which the A-scan is located. The data element in the A-scan having a second (z-) axis coordinate value that most closely matches the value of the fitted quadratic function at the first axis coordinate value at which the A-scan is located, is then selected as the reference data element. The subregion defining module 120 calculates the value of the error measure for the A-scan with respect to the reference data element.

The error measure may take one of many suitable forms. For example, the error measure may, as in the present example embodiment, be a normalised mean squared error (NMSE) of respective deviations of locations of the selected data elements in the A-scan (i.e. those selected in process S210 of FIG. 7) from the location of the reference data element in the A-scan. The NMSE provides the advantage of allowing a common threshold for the entire C-scan volume to be specified. As another example, the error measure may be a sum of absolute deviations of locations of the selected data elements in the A-scan from the location of the reference data element in the A-scan. As a yet further example, the error measure may be a sum of squared deviations of locations of the selected data elements in the A-scan from the location of the reference data element in the A-scan.

FIG. 9 shows a bar graph 730 of the values of the NMSE that have been calculated for the A-scans in the B-scan 210-1, as a function of A-scan location in the B-scan 210-1. In FIG. 9, the bar graph 730 is superimposed on the illustration of the B-scan 210-1, with the bars of the bar graph 730 extending down from zero the top edge of the B-scans 210-1. The lengths of the bars in FIG. 9 represent respective values of the NMSE, and have been scaled by a common scaling factor so that the bar graph 730 fits within the B-scan 210-1 without obscuring the selected data elements 710.

Referring to FIG. 10, in process S223, the subregion defining module 120 compares each value of the NMSE with a threshold error value, and determines whether the value of the NMSE exceeds the threshold error value.

In process S224 of FIG. 10, the subregion defining module 120 generates a modified selection of data elements 810 (see FIG. 11) in the B-scan 210-1 by selecting, for each A-scan in the B-scan 210-1 having a calculated value of the error measure that is greater than the threshold error value, only the data elements from the data elements in the A-scan that have been selected in process S210 of FIG. 7 and are below the reference data element in the A-scan. Selected data elements of an A-scan that have been selected in process S210 of FIG. 7 and are above the reference data element selected for that A-scan (i.e. have smaller values of the z-axis coordinate than the z-axis coordinate of the data element selected for that A-scan) are not included in the modified selection of data elements, as illustrated in FIG. 11.

Figure 11:
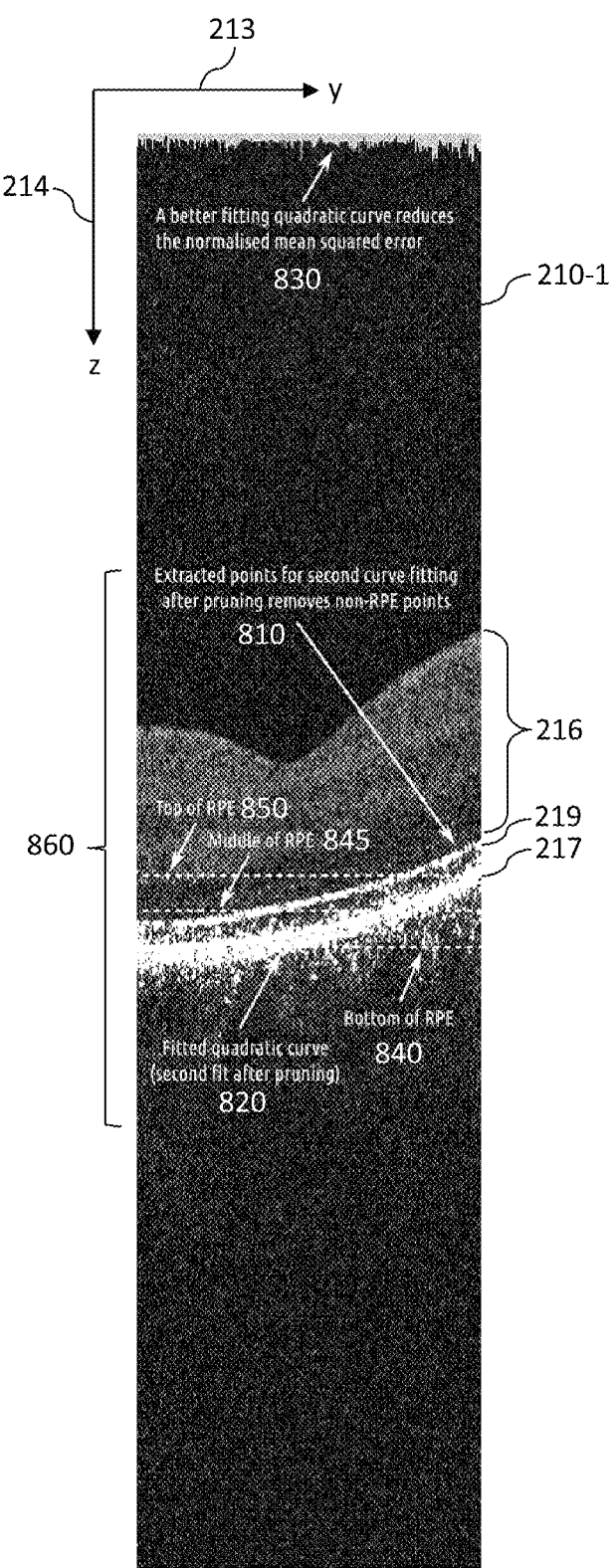
FIG. 11 shows an example of data elements of a modified selection made from the data elements of the B-scan shown in FIG. 3A by the subregion defining module of the example embodiment.

Data elements 810 of the modified selection taken from the data elements of the B-scan 210-1 are shown in FIG. 11. As shown in FIG. 11, the data elements in the modified selection include those representing the RPE but not those representing the NFL.

In process S225 of FIG. 10, the subregion defining module 120 fits a quadratic function to the spatial distribution within the B-scan 210-1 of the modified selection of data elements selected in process S224 of FIG. 10. The quadratic function fitted in process S225 of FIG. 10 is represented by quadratic curve 820 in FIG. 11. As shown in FIG. 11, the quadratic curve 820 is a much closer fit to the representation 217 of the RPE than the quadratic curve 720 shown in FIG. 9, as a large number of data elements from region 216, including the representation of the NFL, have not been included in the modified selection of data elements 810 made in process S224 of FIG. 10. As a result, the bar graph 830, which is superimposed on the B-scan 210-1 in FIG. 11 and shows how values of the NMSE calculated using the quadratic curve 820 and the modified selection of data elements 810 vary across the B-scans 210-1 (using the same vertical (z-axis) scaling as in FIG. 9), illustrates that these NMSE values are much lower across the B-scan 210-1. As a result of performing process S225 in FIG. 10, values of coefficients $a_2$, $b_2$, and $c_2$ to satisfy the equation $z=a_2y^2+b_2y+c_2$ are determined by the subregion defining module 120.

At this stage, the subregion defining module 120 may, as before, evaluate a statistical measure for goodness-of-fit of the quadratic function (fitted in process S225) to the spatial distribution of the modified selection of data elements in the B-scan 210-1, and generate a flag which is associated with the B-scan 210-1 and indicates that the B-scan 210-1 should be inspected more thoroughly, in case the poor curve fitting is caused by a disease that has distorted the RPE so that its shape deviates from the parabolic form that is expected for all healthy eyes. For instance, Choroidal Neo-Vascularisation (CNV) and Age-related Macular Degeneration (AMD) are diseases that could distort the shape of the retina, and therefore the shape of the RPE. The flag generated by the subregion defining module 120 may cause a warning (in the form of a graphic displayed on a display (e.g. LCD screen) connected to the apparatus 100, or an audio signal emitted by a speaker connected to the apparatus 100, for example) to be notified to a user of the apparatus 100, to prompt the user to inspect the B-scan 210-1 for signs of disease. The warning may be notified to the user either at the time of process S225 of FIG. 10 being performed or later, when the repeat B-scans 200 or OCTA data 500 generated therefrom are being inspected by the user, for example.

Provided that the fit of the quadratic function to the spatial distribution of the modified selection of data elements is satisfactory (which may be determined by evaluating a goodness-of-fit metric (e.g. $R^2$ or one of the other metrics mentioned above, for example) for the fitted function, and determining that the fit is satisfactory when the evaluated goodness-of-fit metric exceeds a predetermined threshold, for example), the function coefficients $a_2$, $b_2$, and $c_2$ acquired by the subregion defining module 120 in process S225 of FIG. 10 can be used to calculate a reference coordinate along the z-axis of the B-scan 210-1 that is indicative of a location of the RPE along this axis of the B-scan 210-1. To estimate the top extent of the RPE in the B-scan 210-1, the maximum of $z'_1$ and $z'_2$ is taken, where $z'_1=c_2$ and $z'_2=a_2\cdot(w-1)^2+b_2\cdot(w-1)+c_2$ are respectively the estimated RPE locations for the left-most (y=0) and right-most (y=w−1) columns of the B-scan 210-1. As before, to estimate the bottom extent of the RPE in the B-scan 210-1, the value of z for a column of the B-scan 210-1, where the derivative of the quadratic curve is minimum, is obtained. For healthy retinas, because of the positive curvature of the retina, the minimum point will occur at $y=-b_2/(2\cdot a_2)$. The subregion defining module 120 calculates the reference coordinate along the z-axis of the B-scan 210-1 as a mean of the top and bottom extents of the RPE in the B-scan 210-1.

More generally, the subregion defining module 120 may use the fitted function to calculate the respective reference coordinate along the second axis of the B-scan 210-1 in process S225 of FIG. 10 by determining a maximum value of the fitted function in an interval along the first axis spanned by the A-scans of the B-scan 210-1, determining a minimum value of the fitted function in the interval along the first axis, and calculating, as the reference coordinate, a mean of the maximum value and the minimum value.

In process S227 of FIG. 10, the subregion defining module 120 defines the subregion of interest in the B-scan 210-1 as a subregion of the B-scan 210-1 having a predetermined size and a predetermined offset along the z-axis of the B-scan 210-1 relative to the reference coordinate calculated in process S226 of FIG. 10. The subregion of interest is shown at 860 in FIG. 11. The size of the region of interest 860 along the z-axis of the B-scan 210-1 and the offset of the region of interest 860 relative to the reference coordinate along the z-axis may be predetermined from common knowledge of the anatomy of the eye and, in particular, how the vasculature in the retina is typically distributed relative to the RPE in the depth direction of the retina. In this way, the subregion defining module 120 may define a rectangular subregion of interest 860 in the form of a band extending across the B-scan 210-1, whose upper edge 840 and lower edge 850 are parallel to the y-axis of the B-scan 210-1 and span the B-scan 210-1, the band having a size along the z-axis of the B-scan 210-1 and a location along the z-axis of the B-scan 210-1 such that it contains OCT data acquired from the second subregion of the imaged region of the eye discussed above, which contains the retinal vasculature of interest.

The cropping module 130 may define the upper edge 840 to be a predefined number, α, of pixels above the reference coordinate, and the lower edge 850 to be a predefined number, β, of pixels below the reference coordinate. Here, a and B are user configurable parameters. They may, however, alternatively be determined using a specified top/bottom ratio (i.e. a ratio of the distance between the reference coordinate and the top of the subregion of interest 860, to the distance between the reference coordinate and the bottom of the subregion of interest 860) and a specified height of the region of interest 860. In other words, the required height of the region of interest 860 (i.e. the cropped height of the B-scan) may be specified, and a and B may be determined to match the specified top/bottom ratio.

In the present example embodiment, a modified selection of data elements has been used only once for practical reasons, as a trade-off between reduced computation and required curve fitting accuracy. This refinement may, however, be performed more than once, so that more non-RPE data elements are discarded using quadratic curves fitted to subsequently selected data elements.

Referring again to FIG. 7, in step S230 of FIG. 7, the cropping module 130 generates the respective cropped B-scan 310-1 by cropping the B-scan 210-1 to leave only the subregion of interest 860. In other words, the respective cropped B-scan 310-1 is generated by removing the unwanted outer region of the B-scan 210-1 which extends upward from the upper edge 840 of the subregion of interest 860, and the unwanted outer region of the B-scan 210-1 which extends downward from the lower edge 850 of the subregion of interest 860.

In optional process S240 in FIG. 7, the cropping module 130 adjusts the size of the cropped B-scan 310-1 to a predetermined size, by a process which will now be described with reference to FIG. 12.

In process S242 of FIG. 12, the cropping module 130 determines whether the defined subregion of interest 860 defined in process S227 of FIG. 10 extends along the first axis (or the second axis) of the B-scan 210-1 to an edge of the B-scan 201-1.

In process S244 of FIG. 12, the cropping module 130 determines whether the size of the cropped B-scan 130-1 along the first axis (or the second axis, as the case may be) is smaller than a predetermined size.

In a case where the subregion of interest 860 has been determined in process S242 of FIG. 12 to extend along the first axis (or the second axis, as the case may be) to the edge of the B-scan 120-1, and the size of the cropped B-scan 130-1 along the first axis (or the second axis, as the case may be) has been determined to be smaller than the predetermined size in process S244 of FIG. 12, then in process S246 of FIG. 12 the cropping module 130 increases the size of the cropped B-scan 130-1 to the predetermined size by expanding the cropped B-scan 130-1 along the first axis (or the second axis, as the case may be) to have additional data elements (padding) whose data element values are based on a noise profile calculated from the B-scan 120-1.

To generate the noise profile, the cropping module 130 may sample a region of the B-scan 210-1 whose location depends on where the padding is to be applied. If the padding is required at the top of an A-scan, the cropping module 130 may generate the noise profile by sampling a region in the vitreous humor that does not contain biological artefacts such as "floaters". Image processing can be used to define such as region. For padding at the bottom of an A-scan, the cropping module 130 may perform a similar sampling of the choroidal region, and ensure that the region used to generate the noise profile is also devoid of artefacts such as the choroid.

As an alternative, the cropping module 130 may simply maintain for each cropped B-scan 130-1 regions where information is missing (pixels that required padding). These regions can then be used by follow-on algorithms to either discard, or avoid using, the corresponding pixel values during computations.

To recap, there has been described in the foregoing an apparatus 100 according to an example embodiment, which allows OCTA data-generating software to fix large axial shifts in OCT B-scans while also reducing the size of the OCTA volume for faster processing and reduced memory consumption. Conventional OCTA data-generating software typically uses registration to align B-scan repeats before OCTA signals are calculated from the repeat frames. Depending on the size of the original B-scan, this can take a long time, and with large axial shifts, the registration algorithm could fail to converge. In accordance with the example embodiment, these issues are addressed by providing a pre-registration process by which a well-aligned set of partial B-scans, each having the retina in the middle, is obtained. The alignment can be improved further through image registration of consecutive partial B-scans. Finally, because the original B-scans were cropped to produce the retina-centred OCT volume, the new volume contains all of the information required for detecting OCTA flow signals, while all of the less relevant pixels without OCTA flow signals (such as vitreous humour and deeper choroid) were discarded during cropping. This reduction in the number of voxels in the pre-processed OCT volume reduces the memory and computational requirements of the subsequent OCTA data-generating algorithm.

Modifications and Variations

Various modifications may be made to the embodiment and its variants described above.

For example, the order of some of the processes in the described flow diagrams may be changed. For instance, in FIG. 12, the order in which processes S242 and S244 are performed may be reversed.

Furthermore, process S210 of FIG. 7 described above, by which the selection module 110 of the present example embodiment selects the subset of the data elements distributed along the representation of the RPE in the B-scan 210-1, has been given by way of example only, and that this selection may be performed in other ways. For example, the selection module 110 may alternatively be arranged to select, from data elements of the B-scan 210-1, a (proper) subset of the data elements such that data elements in the subset are distributed along a representation of the anatomical feature (e.g. the RPE) in the B-scan 210-1 by using a retinal layer segmentation algorithm to segment the B-scan 210-1 into a plurality of retinal layers, identifying a predefined retinal layer in the plurality of retinal layers (into which the B-scan 210-1 has been segmented by the retinal layer segmentation algorithm), and selecting, for the subset, data elements in the identified retinal layer. The retinal layer segmentation algorithm may be one of the various kinds of image classification algorithm that have been used to automatically segment an OCT retinal image into distinct retinal layers. A review of such algorithms is provided in "A Review of Algorithms for Segmentation of Optical Coherence Tomography from Retina" by R. Kafieh et al, J Med Signals Sens. 2013 January-March; 3(1): 45-60, which is incorporated by reference herein. The retinal layer segmentation algorithm may, for example be any kind of algorithm for semantic segmentation, which provides a probabilistic output to an m-class classification task. The retinal layer segmentation algorithm may, for example, comprise a convolutional neural network (CNN), a Gaussian Mixture model, a Random Forest, a Bayesian classifier or a Support Vector Machine. In such cases, data elements identified as belonging (most probably) to the RPE become the selected subset of data elements in the method performed by a variant of the apparatus 100 of the example embodiment.

As a further alternative to the implementation in the present example embodiment of step S210 in FIG. 7, the selection of a subset of the data elements such that the selected data elements are distributed along a representation of the anatomical feature in the B-scan may be achieved by use of any well-known edge detection technique. Specifically, an image edge detection method may be used to identify prominent changes in reflectance in the B-scan 210-1, which in FIG. 9 may appear at the lower boundary of the RPE 217, the upper boundary of the RPE 217, the lower boundary of the inner/outer segment junction 219, the upper boundary of the inner/outer segment junction 219 (i.e. the lower boundary of the region 216), and the upper boundary of the region 216. The upper and lower boundaries of the RPE 217 then may be identified using the results of the edge detection, and data elements in between the identified boundaries may be selected for the subset. Alternatively, data elements arranged along one of the boundaries of the RPE may be selected for the subset. The identification of one or both boundaries of the RPE in the edge detection results may be achieved in any suitable way, for example by taking the lowest edge in the B-scan 210-1 as the lower boundary of the RPE. The image edge detection method used may be search-based or zero-crossing based, and may be performed using image processing kernels. For example, the method may be one of Canny, Laplacian, Laplacian of Gaussian, Prewitt, Sobel or Robert edge detection. It may also use a machine learning based edge detection method. Further, pre-processing techniques may be used before the edge detection, such as edge thinning or noise removal.

The data processing techniques used in the example embodiment and the variants thereof described above are applicable not only to retinal OCT scans but more generally to repeat OCT B-scans of other body parts that can be processed to generate OCTA data that provides a representation of vasculature in the body part. For example, human or animal skin may be taken as another example of a body part whose repeat OCT B-scans may be processed using known OCTA data-generating techniques to generate OCTA data representing vasculature in a region of the skin, for example the dermis or hypodermis. Repeat OCT B-scans of the skin, which, for example, cover the epidermis and the dermis, may be processed in a similar way of the retinal B-scans of the example embodiment described above. In this case, the boundary between the dermis and the epidermis, which is usually manifested in the B-scan as a boundary between a region of the B-scan representing the epidermis and an underlying, significantly lighter or significantly darker region of the B-scan representing the dermis, may be taken as the anatomical feature discussed above (in place of the RPE or other layer of the retina).

The example aspects described herein avoid limitations, specifically rooted in computer technology, relating to conventional methods and systems for processing OCT B-scans to generate OCT angiography (OCTA) data, which usually include a pre-processing stage in which an image registration algorithm is used to compensate for axial offsets between the repeat B-scans. Such conventional methods and systems are unduly demanding on computer resources. By virtue of the example aspects described herein, on the other hand, OCTA data can be generated in a manner that may require relatively less computer processing and memory resources than those required by the conventional systems/ methods, thereby enabling the OCTA data generation to be performed in a more highly computationally- and resource-efficient manner relative to the conventional systems/methods. Also, by virtue of the foregoing capabilities of the example aspects described herein, which are rooted in computer technology, the example aspects described herein improve computers and computer processing/functionality, and also improve the field(s) of at least OCT angiography and data processing, and the processing of OCT image data.

Some of the embodiments described above are summarised in the following examples E1 to E12:

E1. An apparatus (100) for processing repeat B-scans (200) of an imaged region of a body part acquired by an optical coherence tomography, OCT, imaging apparatus, the imaged region including an anatomical feature confined to a first subregion of the imaged region and vasculature of interest confined to a second subregion of the imaged region, to generate cropped B-scans (300) for use in generating OCT angiography data (500) which provides a representation of the vasculature of interest, the apparatus (100) comprising:

a selection module (110) arranged to process each B-scan (210-1) of the repeat B-scans (200) by selecting, from data elements of the B-scan (210-1), a respective subset of the data elements such that the selected data elements are distributed along a representation (217) of the anatomical feature in the B-scan (210-1);

a subregion defining module (120) arranged to process each B-scan (210-1) of the repeat B-scans (200) by using the subset of data elements, which has been selected by the selection module (110) from the data elements of the B-scan (210-1), to define a respective subregion of interest (860) in the B-scan (210-1), the respective subregion of interest (860) including OCT data acquired from the second subregion which contains the vasculature of interest; and a cropping module (130) arranged to generate cropped B-scans (300) by cropping each B-scan (210-1) of the repeat B-scans (200) to leave in the B-scan the respective subregion of interest (860) defined for the B-scan by the subregion defining module (120).

E2. The apparatus (100) according to E1, wherein
the body part comprises an eye,
the imaged region of the body part comprises a retina of the eye, and
the anatomical feature comprises an anatomical layer of the retina.

E3. The apparatus (100) according to E2, wherein
the anatomical layer of the retina is a retinal pigment epithelium, RPE, of the retina, and
the selection module (110) is arranged to select the respective subset of data elements for each B-scan (210-1) of the repeat B-scans (200) by determining whether respective values of data elements in the B-scan (210-1) have a predefined relationship to a threshold value, and selecting, for the subset, data elements whose values have the predefined relationship to the threshold value, the threshold value being set such that at least some of the selected data elements are distributed along a representation (217) of the RPE in the B-scan (210-1).

E4. The apparatus (100) according to E3, wherein the selection module (110) is arranged to process each B-scan (210-1) of the repeat B-scans (200) to calculate the threshold value from data element values in the B-scan (210-1) such that there is only a predetermined number of the data elements above a number, k, of standard deviations from a mean of the data element values in the B-scan (210-1), wherein k is set such that at least some of the selected data elements are distributed along the representation (217) of the RPE in the B-scan (210-1), the selection module (110) being arranged to calculate the threshold value by modelling the data element values in the B-scan (210-1) to be distributed in accordance with a predetermined type of statistical distribution.

E5. The apparatus (100) according to any one of E1 to E4, wherein each B-scan (210-1) comprises an array of A-scans that are arrayed along a first axis (213) of the B-scan (210-1), each of the A-scans comprising data elements arrayed along a second axis (214) of the B-scan,
the anatomical feature comprises an anatomical layer of the body part that extends over the first subregion of the imaged region, and
the subregion defining module (120) is arranged to process each B-scan (210-1) of the repeat B-scans (200) by using the subset of data elements, which has been selected by the selection module (110) from the data elements of the B-scan, to define a respective subregion of interest (860) in the B-scan, by:
fitting a function to a distribution within the B-scan of the selected data elements;
using the fitted function to calculate a respective reference coordinate along the second axis (214) of the B-scan (210-1); and
defining the respective subregion of interest (860) in the B-scan (210-1) as a subregion of the B-scan (210-1) having a predetermined size and a predetermined offset along the second axis (214) of the B-scan (210-1) relative to the calculated respective reference coordinate.

E6. The apparatus (100) according to E5, wherein the body part comprises an eye, the imaged region of the body part comprises a retina of the eye, the anatomical layer comprises a retinal pigment epithelium, RPE, of the retina, and the function is a quadratic function.

E7. The apparatus (100) according to E3 or E4, wherein each B-scan (210-1) comprises an array of A-scans that are arrayed along a first axis (213) of the B-scan (210-1), each of the A-scans comprising data elements arrayed along a second axis (214) of the B-scan (210-1), and the subregion defining module (120) is arranged to process each B-scan (210-1) of the repeat B-scans (200) by using the subset of data elements, which has been selected by the selection module (110) from the data elements of the B-scan (210-1), to define a respective subregion of interest (860) in the B-scan (210-1), by:

fitting a function to a distribution within the B-scan (210-1) of the selected data elements;

calculating, for each A-scan in the B-scan (210-1), a respective value of an error measure for the selected data elements in the A-scan that is indicative of a distribution of the selected data elements along the A-scan, the respective value of the error measure being calculated for each A-scan in the B-scan (210-1) with reference to a respective data element in the A-scan corresponding to a value of the fitted function at a coordinate of the A-scan along the first axis (213);

comparing, each A-scan of the B-scan (210-1), the value of the error measure, which has been calculated for the selected data elements in the A-scan, with a threshold error value;

generating a modified selection of data elements in the B-scan (210-1) by selecting, for each A-scan in the B-scan (210-1) having a calculated value of the error measure that is greater than the threshold error value, data elements from the selected data elements in the A-scan that are below the respective data element in the A-scan;

fitting the function to a distribution within the B-scan (210-1) of the modified selection of data elements;

using the function fitted to the distribution within the B-scan (210-1) of the modified selection of data elements to calculate a respective reference coordinate along the second axis (214) of the B-scan (210-1); and defining the respective subregion of interest (860) in the B-scan (210-1) as a subregion of the B-scan having a predetermined size and a predetermined offset along the second axis (214) of the B-scan (210-1) relative to the calculated respective reference coordinate.

E8. The apparatus (100) according to E7, wherein the error measure comprises one of:

a normalised mean squared error of deviations of locations of the selected data elements in the A-scan from a location of a data element in the A-scan corresponding to the value of the fitted function at the coordinate of the A-scan along the first axis (213);

a sum of absolute deviations of locations of the selected data elements in the A-scan from a location of a data element in the A-scan corresponding to the value of the fitted function at the coordinate of the A-scan along the first axis (213); and a sum of squared deviations of locations of the selected data elements in the A-scan from a location of a data element in the A-scan corresponding to the value of the fitted function at the coordinate of the A-scan along the first axis (213).

E9. The apparatus according to E7 or E8, wherein the function is a quadratic function.

E10. The apparatus (100) according to any one of E5 to E9, wherein the subregion defining module (120) is arranged to use the fitted function to calculate the respective reference coordinate along the second axis (214) of the B-scan by:

determining a maximum value of the fitted function in an interval along the first axis (213) spanned by the A-scans of the B-scan (210-1);

determining a minimum value of the fitted function in the interval along the first axis (213); and calculating, as the respective reference coordinate, a mean of the maximum value and the minimum value.

E11. The apparatus (100) according to any one of E1 to E10, wherein each B-scan (210-1) comprises an array of A-scans that are arrayed along a first axis (213) of the B-scan (210-1), each of the A-scans comprising data elements arrayed along a second axis (214) of the B-scan (210-1), and the cropping module (130) is further configured to:

determine whether the defined subregion of interest (860) extends along one of the first axis (213) and the second axis (214) to an edge of the B-scan (210-1);

determine whether a size of the cropped B-scan (310-1) along the one of the first axis (213) and the second axis (214) is smaller than a predetermined size; and in a case where the subregion of interest (860) has been determined to extend along the one of the first axis (213) and the second axis (214) to the edge of the B-scan, and the size of the cropped B-scan (310-1) along the one of the first axis (213) and the second axis (214) has been determined to be smaller than the predetermined size, increase the size of the cropped B-scan (310-1) to the predetermined size by expanding the cropped B-scan (310-1) along the one of the first axis (213) and the second axis (214) to have additional data elements whose data element values are based on a noise profile calculated from the B-scan.

E12. An apparatus (400) for generating optical coherence tomography angiography, OCTA, data (500) which provides a representation of vasculature in an imaged region of a body part, the apparatus (400) comprising:

a receiver module (410) arranged to receive repeat B-scans (200) of the imaged region of the body part acquired by an optical coherence tomography imaging apparatus;

the apparatus (100) according to any one of E1 to E11, which is arranged to process the received repeat OCT B-scans (200) to generate cropped B-scans (300); and an OCTA data generating module (420) arranged to generate the OCTA data (500) by processing the cropped B-scans (300).

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer and that causes processor the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/ storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/ archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The invention claimed is:

1. A non-transitory computer-readable storage medium storing instructions which, when executed by a computer processor, cause the computer processor to perform a method of processing repeat B-scans of an imaged region of a body part acquired by an optical coherence tomography (OCT) imaging apparatus, the imaged region including an anatomical feature confined to a first subregion of the imaged region and vasculature of interest that is confined to a second subregion of the imaged region, to generate cropped B-scans for use in generating OCT angiography (OCTA) data which provides a representation of the vasculature of interest, the method comprising processing each B-scan of the repeat B-scans to generate a respective cropped B-scan by:

selecting, from data elements of the B-scan, a subset of the data elements such that the selected data elements are distributed along a representation of the anatomical feature in the B-scan;

using the selected data elements to define a respective subregion of interest in the B-scan, the respective subregion of interest including OCT data acquired from the second subregion which contains the vasculature of interest; and generating the respective cropped B-scan by cropping the B-scan to leave the subregion of interest in the B-scan.

2. The non-transitory computer-readable storage medium according to claim 1, wherein the body part comprises an eye, the imaged region of the body part comprises a retina of the eye, and the anatomical feature comprises an anatomical layer of the retina.

3. The non-transitory computer-readable storage medium according to claim 2, wherein the anatomical layer of the retina is a retinal pigment epithelium, RPE, of the retina, and the selecting of the subset of data elements comprises determining whether respective values of data elements in the B-scan have a predefined relationship to a threshold value, and selecting, for the subset, data elements whose values have the predefined relationship to the threshold value, the threshold value being set such that at least some of the selected data elements are distributed along a representation of the RPE in the B-scan.

4. The non-transitory computer-readable storage medium according to claim 3, wherein the threshold value is calculated from data element values in the B-scan such that there is only a predetermined number of the data elements above a number, k, of standard deviations from a mean, u, of the data element values in the B-scan, wherein k is set such that at least some of the selected data elements are distributed along the representation of the RPE in the B-scan, the threshold value being calculated by modelling the data element values in the B-scan to be distributed in accordance with a predetermined type of statistical distribution.

5. The non-transitory computer-readable storage medium according to claim 3, wherein each B-scan comprises an array of A-scans that are arrayed along a first axis of the B-scan, each of the A-scans comprising data elements arrayed along a second axis of the B-scan, the selected data elements are used to define a respective subregion of interest in the B-scan relative to the selected data elements by:

fitting a function to a distribution within the B-scan of the selected data elements;

calculating, for each A-scan in the B-scan, a respective value of an error measure for the selected data elements in the A-scan that is indicative of a distribution of the selected data elements along the A-scan, the respective value of the error measure being calculated for each A-scan in the B-scan with reference to a respective data element in the A-scan corresponding to a value of the fitted function at a coordinate of the A-scan along the first axis;

comparing, for each A-scan of the B-scan, the value of the error measure, which has been calculated for the selected data elements in the A-scan, with a threshold error value;

generating a modified selection of data elements in the B-scan by selecting, for each A-scan in the B-scan having a calculated value of the error measure that is greater than the threshold error value, data elements from the selected data elements in the A-scan that are below the respective data element in the A-scan;

fitting the function to a distribution within the B-scan of the modified selection of data elements;

using the function fitted to the distribution within the B-scan of the modified selection of data elements to calculate a respective reference coordinate along the second axis of the B-scan; and defining the respective subregion of interest in the B-scan as a subregion of the B-scan having a predetermined size and a predetermined offset along the second axis of the B-scan relative to the calculated respective reference coordinate.

6. The non-transitory computer-readable storage medium according to claim 5, wherein the error measure comprises one of:

a normalized mean squared error of respective deviations of locations of the selected data elements in the A-scan from a location of a data element in the A-scan corresponding to the value of the fitted function at the coordinate of the A-scan along the first axis;

a sum of absolute deviations of locations of the selected data elements in the A-scan from a location of a data element in the A-scan corresponding to the value of the fitted function at the coordinate of the A-scan along the first axis; or a sum of squared deviations of respective locations of the selected data elements in the A-scan from a location of a data element in the A-scan corresponding to the value of the fitted function at the coordinate of the A-scan along the first axis.

7. The non-transitory computer-readable storage medium according to claim 5, wherein the function is a quadratic function.

8. The non-transitory computer-readable storage medium according to claim 1, wherein each B-scan comprises an array of A-scans that are arrayed along a first axis of the B-scan, each of the A-scans comprising data elements arrayed along a second axis of the B-scan, the anatomical feature comprises an anatomical layer of the body part which is confined to the first subregion of the imaged region, the selected data elements are used to define a respective subregion of interest in the B-scan relative to the selected data elements by:

fitting a function to a distribution within the B-scan of the selected data elements;

using the fitted function to calculate a respective reference coordinate along the second axis of the B-scan; and defining the respective subregion of interest in the B-scan as a subregion of the B-scan having a predetermined size and a predetermined offset along the second axis of the B-scan relative to the calculated respective reference coordinate.

9. The non-transitory computer-readable storage medium according to claim 8, wherein the body part comprises an eye, the imaged region of the body part comprises a retina of the eye, the anatomical layer comprises a retinal pigment epithelium, RPE, of the retina, and the function is a quadratic function.

10. The non-transitory computer-readable storage medium according to claim 8, wherein using the fitted function to calculate the respective reference coordinate along the second axis of the B-scan comprises:

determining a maximum value of the fitted function in an interval along the first axis spanned by the A-scans of the B-scan;

determining a minimum value of the fitted function in the interval along the first axis; and calculating, as the reference coordinate, a mean of the maximum value and the minimum value.

11. The non-transitory computer-readable storage medium according to claim 1, wherein each B-scan comprises an array of A-scans that are arrayed along a first axis of the B-scan, each of the A-scans comprising data elements arrayed along a second axis of the B-scan, and the method further comprises:

determining whether the defined subregion of interest extends along one of the first axis and the second axis to an edge of the B-scan;

determining whether a size of the cropped B-scan along the one of the first axis and the second axis is smaller than a predetermined size; and in a case where the subregion of interest has been determined to extend along the one of the first axis and the second axis to the edge of the B-scan, and the size of the cropped B-scan along the one of the first axis and the second axis has been determined to be smaller than the predetermined size, increasing the size of the cropped B-scan to the predetermined size by expanding the cropped B-scan along the one of the first axis and the second axis to have additional data elements whose data element values are based on a noise profile calculated from the B-scan.

\* \* \* \* \*